United States Patent
Smith

(10) Patent No.: US 8,282,603 B2
(45) Date of Patent: Oct. 9, 2012

(54) VALVE ASSEMBLY INCLUDING DIAMETER REDUCTION STRUCTURE FOR TROCAR

(75) Inventor: Robert C. Smith, Cheshire, CT (US)

(73) Assignee: Tyco Healthcare Group LP, Mansfield, MA (US)

(*) Notice: Subject to any disclaimer, the term of this patent is extended or adjusted under 35 U.S.C. 154(b) by 0 days.

(21) Appl. No.: 12/824,528

(22) Filed: Jun. 28, 2010

(65) Prior Publication Data
US 2010/0331783 A1 Dec. 30, 2010

Related U.S. Application Data

(63) Continuation of application No. 12/202,857, filed on Sep. 2, 2008, now Pat. No. 7,744,569, which is a continuation of application No. 11/097,550, filed on Apr. 1, 2005, now abandoned, which is a continuation-in-part of application No. 10/380,942, filed as application No. PCT/US01/31911 on Oct. 12, 2001, now Pat. No. 7,025,747.

(60) Provisional application No. 60/240,506, filed on Oct. 13, 2000.

(51) Int. Cl.
*A61M 5/178* (2006.01)

(52) U.S. Cl. ......... 604/167.03; 604/167.01; 604/167.04; 604/167.06

(58) Field of Classification Search ............. 604/167.01, 604/167.02, 167.03, 167.04, 167.06, 256
See application file for complete search history.

(56) References Cited

U.S. PATENT DOCUMENTS

| | | |
|---|---|---|
| 4,917,668 A | 4/1990 | Haindl |
| 5,104,383 A | 4/1992 | Shichman |
| 5,127,626 A | 7/1992 | Hilal et al. |
| 5,180,373 A | 1/1993 | Green et al. |
| 5,197,955 A | 3/1993 | Stephens et al. |
| 5,209,736 A | 5/1993 | Stephens et al. |
| 5,209,737 A | 5/1993 | Ritchart et al. |
| 5,242,412 A | 9/1993 | Blake, III |
| 5,304,143 A | 4/1994 | Green et al. |
| 5,308,336 A | 5/1994 | Hart et al. |
| 5,342,315 A | 8/1994 | Rowe et al. |
| 5,350,364 A | 9/1994 | Stephens et al. |
| 5,354,280 A | 10/1994 | Haber et al. |

(Continued)

FOREIGN PATENT DOCUMENTS

WO    WO 93/01850    2/1993

(Continued)

OTHER PUBLICATIONS

European Search Report for EP 06006538, date of completion is Jul. 18, 2006 (5 pages).

*Primary Examiner* — Bhisma Mehta

(57) ABSTRACT

A surgical access device includes a surgical sleeve defining a central longitudinal axis and having a longitudinal passageway to permit passage of a surgical object, and a diameter reduction assembly operably couplable to the surgical sleeve. The diameter reduction assembly includes a structure foundation and at least three stand-off elements mounted to the structure foundation. Each stand-off element is positioned to engage the surgical object and is independently movable relative to the remaining stand-off elements. The at least three stand-off elements are normally biased to a first position which urges the surgical object into general alignment with the central longitudinal axis, and are adapted for distal pivotal movement from the first position to a second position to facilitate passage of the surgical object, and for proximal pivotal movement from the first position to a third position to facilitate withdrawal of the surgical object.

10 Claims, 29 Drawing Sheets

U.S. PATENT DOCUMENTS

| | | | |
|---|---|---|---|
| 5,380,288 A | 1/1995 | Hart et al. |
| 5,388,553 A | 2/1995 | Burke et al. |
| 5,391,153 A | 2/1995 | Haber et al. |
| 5,391,154 A | 2/1995 | Young |
| 5,407,433 A | 4/1995 | Loomas |
| 5,411,483 A | 5/1995 | Loomas et al. |
| 5,443,452 A | 8/1995 | Hart et al. |
| 5,485,553 A | 1/1996 | Kovalick et al. |
| 5,492,304 A | 2/1996 | Smith et al. |
| 5,496,280 A | 3/1996 | Vandenbroek et al. |
| 5,542,931 A | 8/1996 | Gravener et al. |
| 5,545,142 A | 8/1996 | Stephens et al. |
| 5,549,565 A | 8/1996 | Ryan et al. |
| 5,584,850 A | 12/1996 | Hart et al. |
| 5,603,702 A | 2/1997 | Smith et al. |
| 5,628,732 A | 5/1997 | Antoon, Jr. et al. |
| 5,634,908 A | 6/1997 | Loomas |
| 5,693,031 A | 12/1997 | Ryan et al. |
| 5,709,654 A | 1/1998 | Klatz et al. |
| 5,752,938 A | 5/1998 | Flatland et al. |
| 5,782,812 A | 7/1998 | Hart et al. |
| 5,792,113 A | 8/1998 | Kramer et al. |
| 5,803,919 A | 9/1998 | Hart et al. |
| 5,827,228 A | 10/1998 | Rowe |
| 5,871,471 A | 2/1999 | Ryan et al. |
| 5,895,377 A | 4/1999 | Smith et al. |
| 6,083,203 A | 7/2000 | Yoon |
| 6,093,176 A | 7/2000 | Dennis |
| 6,450,992 B1 | 9/2002 | Cassidy, Jr. |
| 6,702,787 B2 | 3/2004 | Pasqualucci et al. |
| 2004/0064100 A1 | 4/2004 | Smith |
| 2004/0236347 A1 | 11/2004 | Karasawa |
| 2005/0010238 A1 | 1/2005 | Potter et al. |
| 2005/0070851 A1 | 3/2005 | Thompson et al. |

FOREIGN PATENT DOCUMENTS

| | | |
|---|---|---|
| WO | WO 02/30305 | 4/2002 |

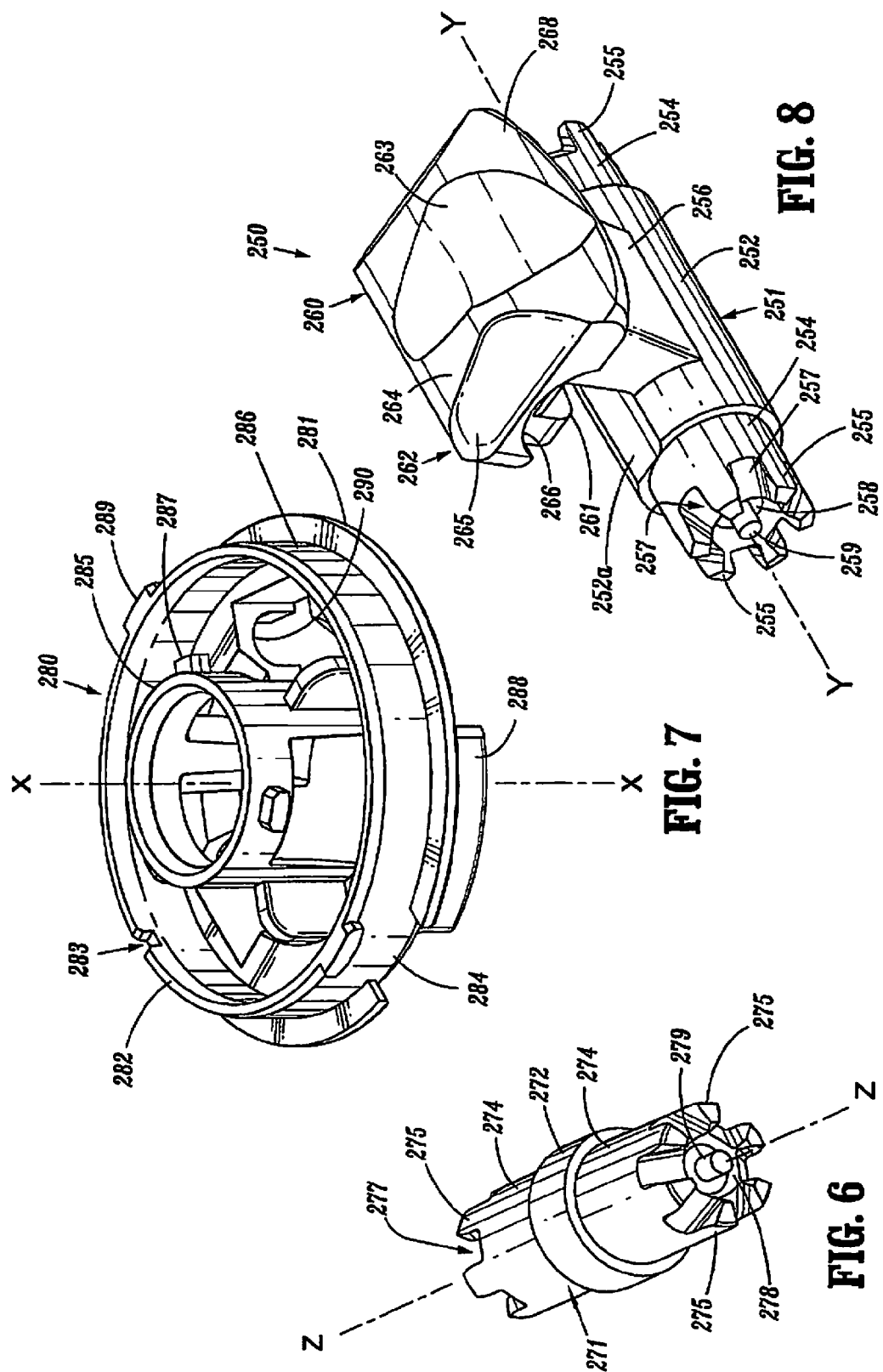

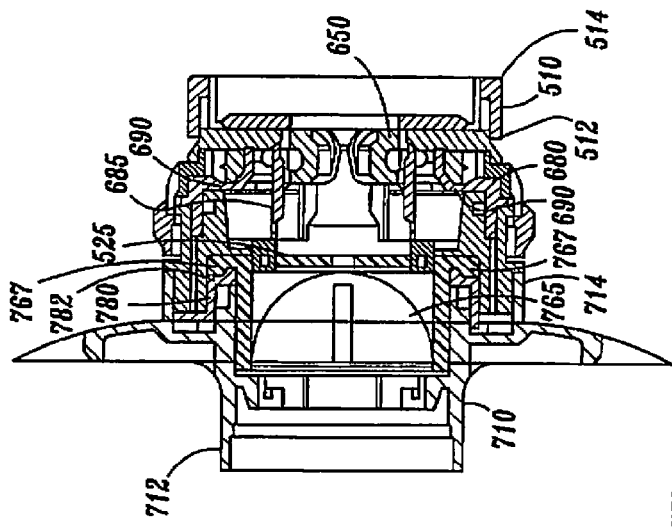
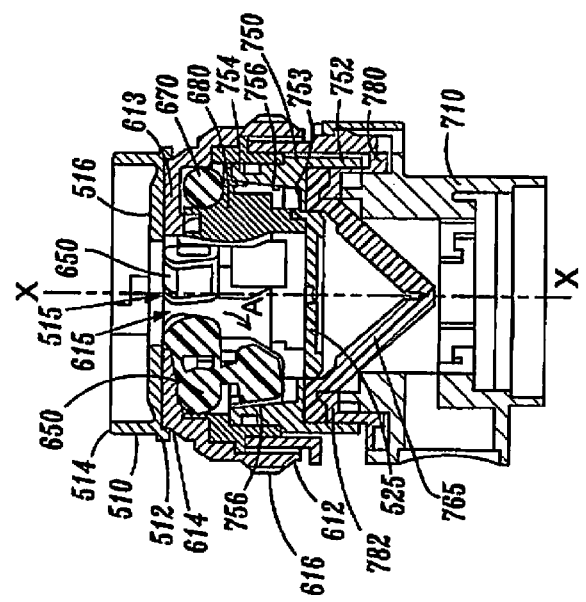
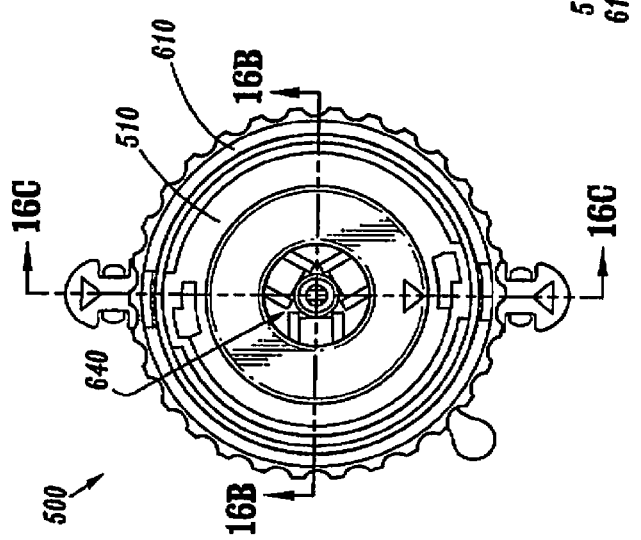

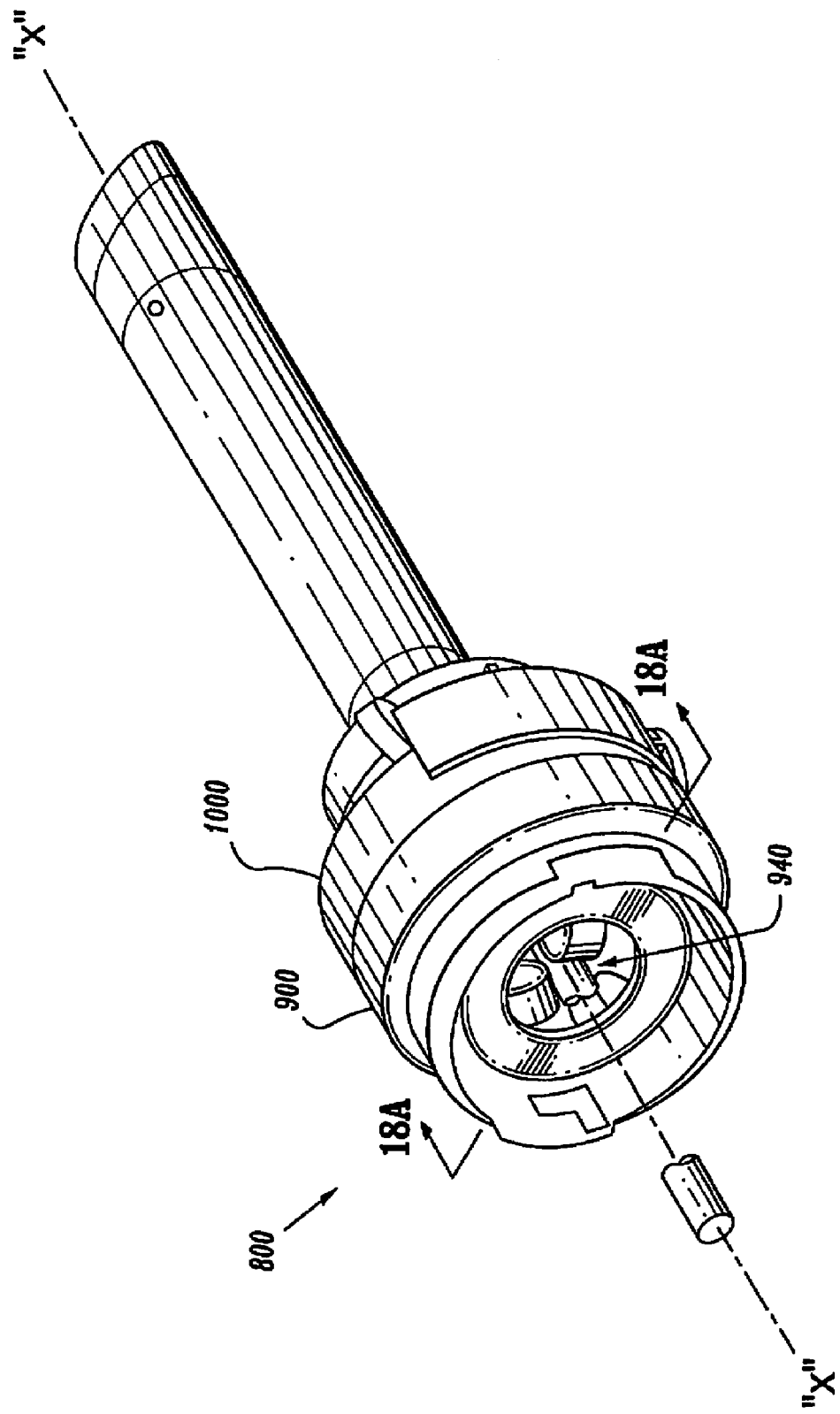

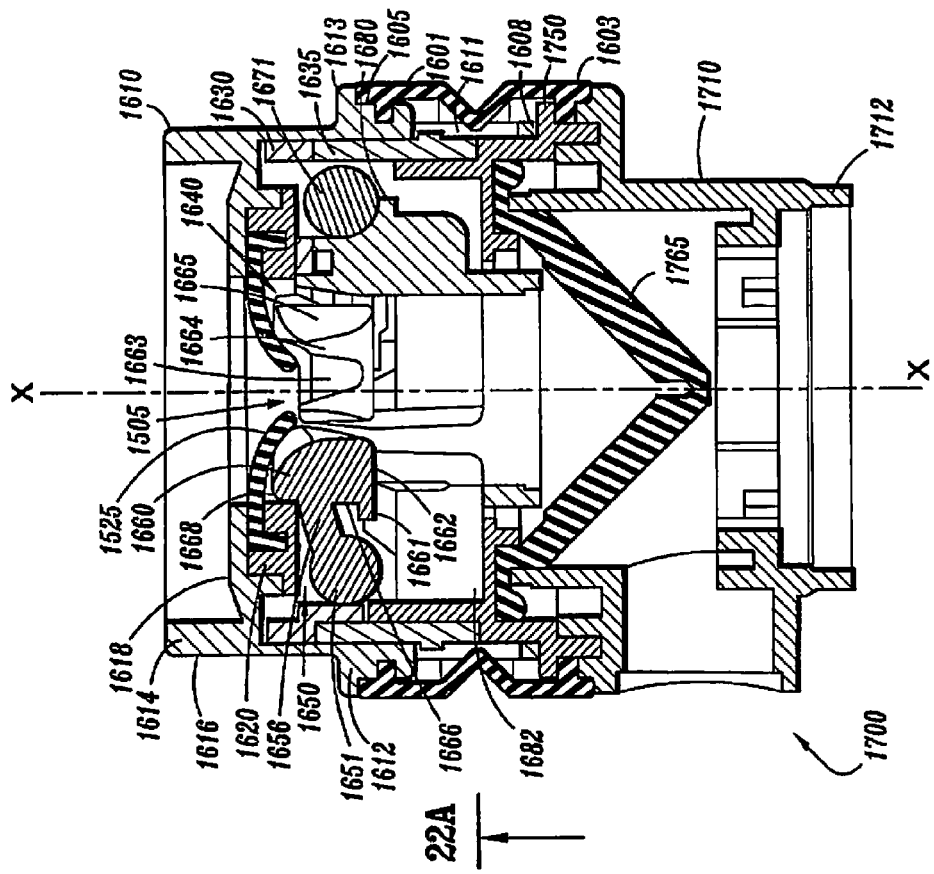
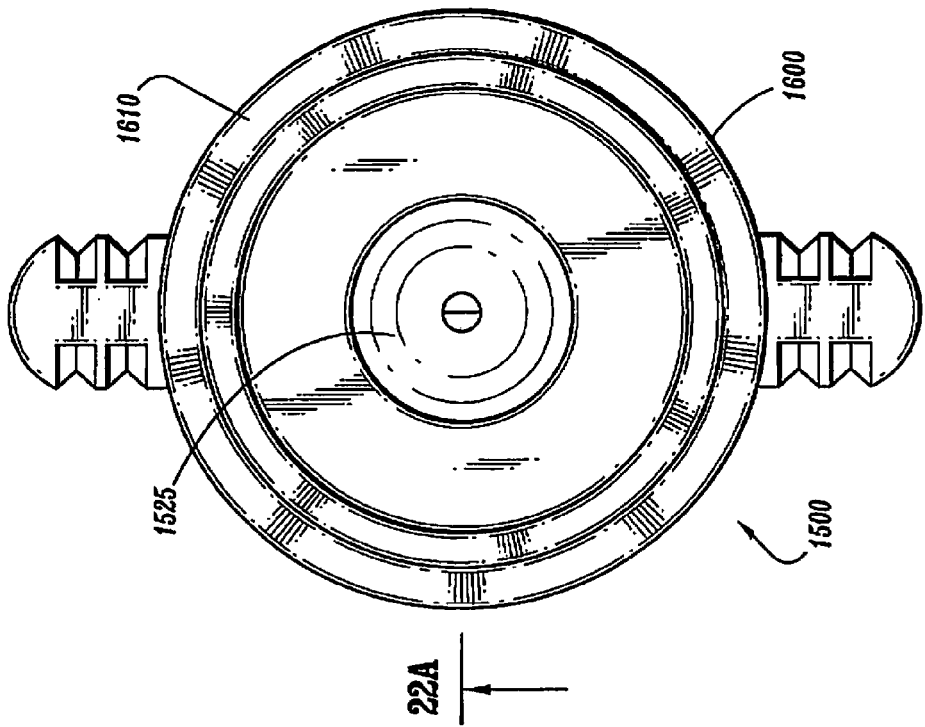

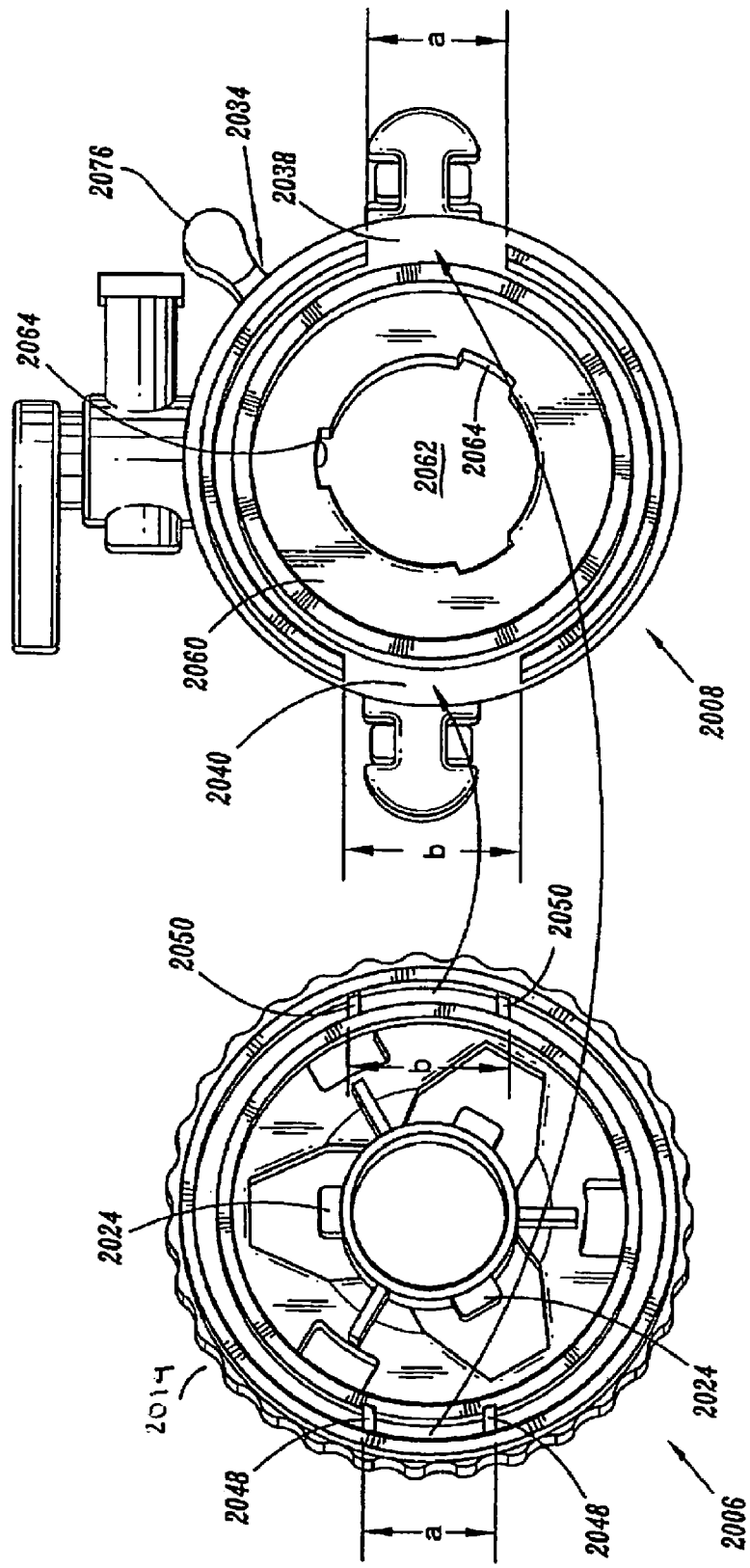

VALVE ASSEMBLY INCLUDING DIAMETER REDUCTION STRUCTURE FOR TROCAR

CROSS REFERENCE TO RELATED APPLICATIONS

This application is a continuation of U.S. patent application Ser. No. 12/202,857, now U.S. Pat. No. 7,744,569, filed Sep. 2, 2008, which is a continuation of U.S. patent application Ser. No. 11/097,550, filed Apr. 1, 2005, now abandoned, which is a continuation-in-part of U.S. patent application Ser. No. 10/380,942, which was a national phase application of International Application No. PCT/US01/31911, filed Oct. 12, 2001, that issued as U.S. Pat. No. 7,025,747 on Apr. 11, 2006, which claims the benefit of U.S. Application Ser. No. 60/240,506, filed Oct. 13, 2000, the entire contents of each application being hereby incorporated by their entireties by reference herein.

BACKGROUND

1. Technical Field

The present disclosure relates to a mechanism for controlling the operable inside diameter of a passageway through a valve assembly of a trocar housing. More particularly, the present disclosure relates to a diameter reduction structure that restricts the movement of small surgical instruments and accommodates large diameter surgical instruments in the passageway of a trocar housing to facilitate the maintenance of a gas tight seal formed by the valve assembly.

2. Background of Related Art

Trocar valve assemblies preferably provide a fluid tight seal about a surgical instrument introduced through the trocar during a minimally invasive surgical procedure. A typical valve assembly includes an outer seal, which can be fixed or floating, in combination with additional inner seals. Fixed outer seals are limited by their ability to sustain a seal when a smaller surgical instrument is moved off-axis relative to a central axis of the trocar. Fixed seals are also limited by their ability to sustain their integrity when the surgical instrument is angulated. Such extreme ranges of motion of smaller diameter surgical instruments within the cannula can create a "cat eye" or crescent shaped gap in the fixed seal that can result in a loss of seal integrity. Additional problems include the flexibility of the seal in maintaining its integrity when both small and large diameter surgical instruments are used.

Devices to restrict the diameter of a passageway in a trocar housing generally require an additional mechanism to be positioned on the proximal end of the trocar housing that restricts the range of motion of small surgical instruments. These diameter reducing devices, however, typically employ additional seals and/or structures that require adjustments by the user to accommodate different sized surgical instruments, thereby complicating the surgical process.

A continuing need exists for a diameter reducing structure that can limit parallel off-axis as well as angular movements of small diameter surgical instruments and accommodate larger diameter surgical instruments without external adjustments.

SUMMARY

In accordance with a preferred embodiment, a surgical seal assembly includes a sleeve housing connected to a surgical sleeve, a seal housing including a seal member having inner portions adapted to permit passage of a surgical instrument in substantial sealed relation therewith, and a manual lock member movably mounted to the sleeve housing. The manual lock member is adapted for movement relative to the seal housing between a first position corresponding to a release position of the seal housing to permit detachment of the seal housing from the sleeve housing and a second position corresponding to a lock position of the seal housing to secure the seal housing to the sleeve housing. The manual lock member is preferably adapted for rotational movement relative to a longitudinal axis of the seal housing to move between the first and second positions thereof.

The manual lock member may include an annular member having at least one locking surface adapted to engage at least one corresponding locking tab of the seal housing upon movement of the manual lock member to the second position. The annular member defines a central aperture for permitting passage of the object. Preferably, the annular member defines a plurality of internal mounting recesses adjacent the central aperture and in communication therewith, and the seal housing has a plurality of locking tabs corresponding to the mounting recesses. The mounting recesses are in general alignment with the locking tabs of the seal housing when in the first position of the manual lock member to receive the locking tabs. The mounting recesses are thereafter displaced from the locking tabs upon movement of the manual lock member to the second position thereof. The manual lock member may include a manual grip member depending radially outwardly relative to the longitudinal axis of the seal housing. The manual grip member is dimensioned and configured for engagement by the surgeon.

The surgical seal assembly may include at least two stand-off elements mounted within the seal housing distal of the seal member. The stand-off elements are adapted for pivotal movement between an initial position and a pivoted position to permit passage of the surgical object. The stand-off elements may be normally biased to the initial position to restrict off-axis movement of the surgical object with respect to a longitudinal axis of the seal housing. The at least two stand-off elements are preferably operatively coupled such that movement of at least one of the stand-off elements between the initial and pivoted positions causes corresponding movement of the other stand-off elements.

The sleeve housing may be adapted for connection to a cannula housing of a cannula assembly.

In another preferred embodiment, a surgical system includes a cannula assembly including a cannula housing and a cannula sleeve extending from the cannula housing. The cannula sleeve defines a longitudinal axis and has a longitudinal passageway to permit passage of a surgical instrument. The surgical system further includes a surgical seal assembly incorporating first and second seal subassemblies. The first seal subassembly includes a first housing having a seal member defining inner portions adapted to permit passage of a surgical object in substantial sealed relation therewith. The second seal subassembly includes a second housing adapted for mounting to the cannula housing. A manual lock member is adapted for movement between a first position corresponding to a release position of the first subassembly to permit removal of the first subassembly from mounting to the second subassembly, and a second position corresponding to a lock position of the first subassembly to secure the first subassembly to the second subassembly. Preferably, the second subassembly includes the manual lock member.

The manual lock member may be adapted for rotational movement relative to the longitudinal axis to move between the first and second positions thereof. One of the first and second seal assemblies includes a locking latch and the other of the first and second seal subassemblies includes a corresponding locking surfaces. The locking latch and the locking surface cooperate to secure the first seal subassembly to the second seal subassembly upon movement of the manual lock member to the second position thereof. The other of the first and second seal subassemblies includes a locking recess dimensioned for receiving the locking latch when the manual lock member is in the first position whereby upon rotation of the manual lock member to the second position the locking latch cooperatively engages the locking surface. Preferably, the first seal subassembly includes the locking latch and the second seal subassembly includes the locking recess and the locking surface. The first seal subassembly preferably includes a plurality of locking latches and the second seal subassembly includes a plurality corresponding locking recesses for receiving the locking latches.

The second subassembly may include a zero closure valve adapted to open to permit passage of the surgical instrument and to substantially close in the absence of the surgical instrument.

A method for performing a surgical procedure is also disclosed. The method includes the steps of:

providing an access assembly including an access housing and an access sleeve operatively connected to the access housing;

mounting a seal assembly to the access housing with the seal assembly including a seal housing and a seal member mounted relative to the seal housing, the seal member including inner portions adapted to form a substantial seal about a surgical object introduced therethrough; and securing the seal housing relative to the access housing by moving a manual lock member associated with the access housing to cause corresponding structure of the access housing and the seal housing to cooperatively engage in secured relation therewith.

BRIEF DESCRIPTION OF THE DRAWINGS

Preferred embodiments of the presently disclosed trocar diameter reduction structures for trocar are described herein with reference to the drawings, wherein:

FIG. 6 is a close-up perspective view of a linking member in accordance with the disclosure of FIG. 1;

FIG. 7 is a close-up perspective view of a distal end portion of the diameter reduction structure foundation element in accordance with the disclosure of FIG. 1;

FIG. 8 is a close-up perspective view of a stand off in accordance with the disclosure of FIG. 1;

FIG. 16A is a top view of a second embodiment of a valve and diameter reduction structure constructed in accordance with the present disclosure;

FIG. 16B is a cross-sectional view of FIG. 16A along lines 16B-16B showing a representative movement of one stand off member of the diameter reduction structure;

FIG. 16C is a cross-sectional view of FIG. 16A along lines 16C-16C showing the diameter reduction structure in a first position;

FIG. 17 is a perspective view of a proximal end of a third embodiment of a diameter reduction structure for trocar constructed in accordance with the present disclosure;

FIG. 21 is a top view of a sixth embodiment of a valve assembly and diameter reduction structure for trocar having a movable diameter reduction assembly constructed in accordance with the present disclosure;

FIG. 22A is a cross-sectional view of the valve assembly and diameter reduction structure for trocar stand for trocar of FIG. 21 along line 21A-21A;

FIG. 28 is a view illustrating the mounting tabs of the first seal subassembly in accordance with the embodiment of FIGS. 24-27;

FIG. 29 is a view illustrating the mounting recesses of the second seal subassembly for receiving the mounting tabs of the first seal subassembly in accordance with the embodiment of FIGS. 24-28;

DETAILED DESCRIPTION OF THE PREFERRED EMBODIMENTS

The present disclosure contemplates the introduction into a body of a patient a trocar adapted for receiving all types of surgical instruments including clip appliers, graspers, dissectors, retractors, staplers, laser fibers, endoscopes, as well as electrosurgical cutting, coagulating, and ablation devices, and the like. All such objects are referred to herein as "instruments".

Figure 1:
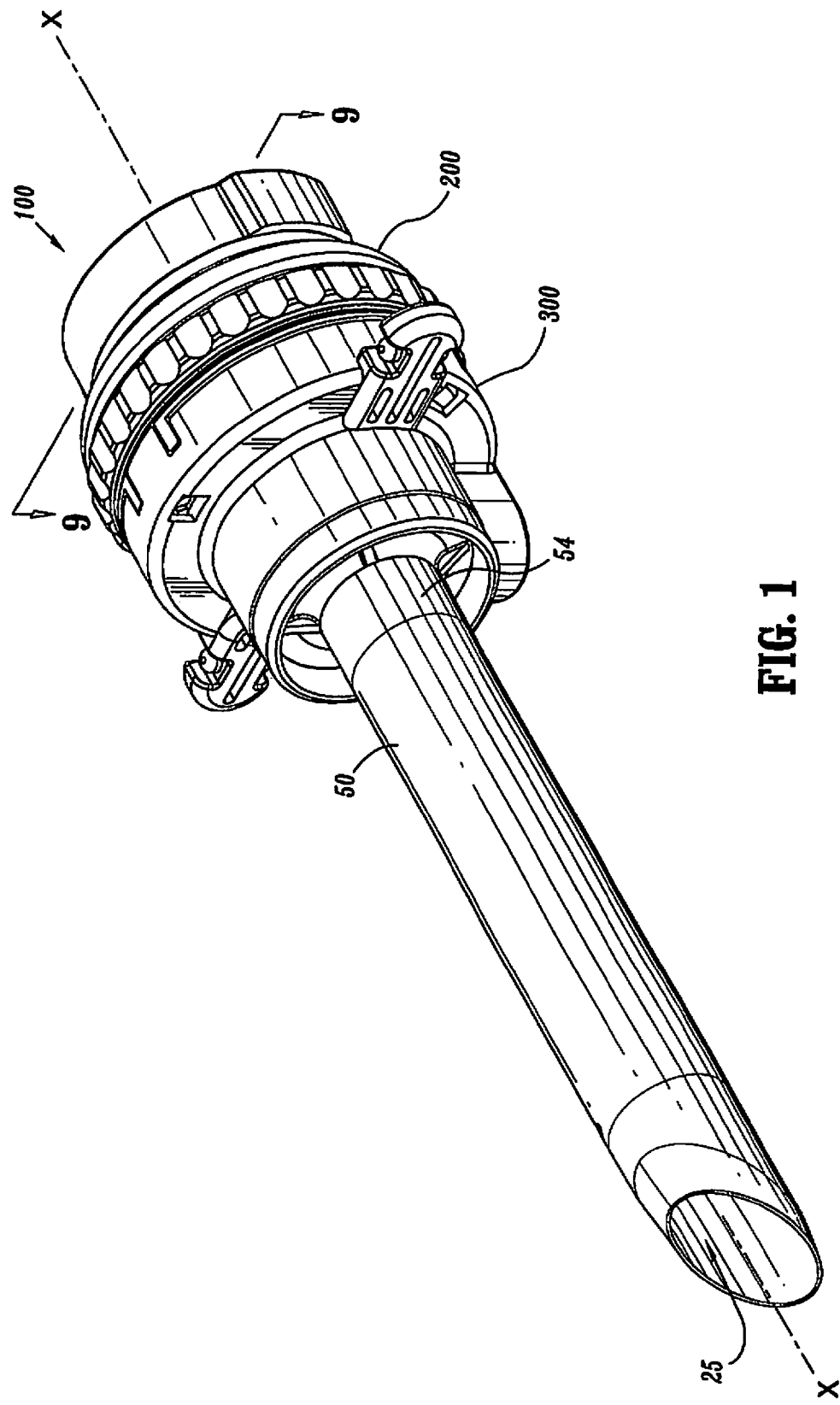
FIG. 1 is a perspective view of one preferred embodiment of a valve assembly and diameter reduction structure for trocars constructed in accordance with the present disclosure.

Referring now in specific detail to the drawings in which like referenced numerals identify similar or identical elements throughout the several views, and initially to FIG. 1, a novel valve assembly and diameter reduction structure for trocar 100 is shown constructed in accordance with a preferred embodiment of the present disclosure and intended to be used in combination with a conventional trocar assembly and cannula 50 defining a passageway 25 aligned with a central longitudinal axis-X. Passageway 25 defines a first operational area.

Valve assembly and diameter reduction structure 100 includes diameter reduction assembly 200 located adjacent a proximal end portion and valve assembly 300 located adjacent a distal end portion. The diameter reduction assembly 200 of the present disclosure, either alone or in combination with valve assembly 300 provides a seal between a cavity formed in the patient and the outside atmosphere during and subsequent to insertion of an instrument through cannula 50. Moreover, valve assembly and diameter reduction structure 100 is capable of accommodating instruments of varying diameter, e.g. from ranges such as 5 mm to 12 mm, by providing a gas tight seal with each instrument during surgical procedures. The flexibility of the present valve assembly and diameter reduction structure 100 to retain a fluid tight seal greatly facilitates endoscopic surgery where a variety of instruments having differing diameters are often needed during a single surgical procedure and off axis movements as well as small tool surgical angulation is employed.

Valve assembly and diameter reduction structure 100 is preferably detachably mountable to a proximal end 54 of cannula 50. During surgery, the surgeon can remove the diameter reduction assembly 200 from valve assembly 300 at any time during the surgical procedure and, similarly, mount diameter reduction assembly 200 to valve assembly 300 to reconfigure diameter reduction structure and valve assembly 100. In addition, diameter and valve assembly 100 may be readily adapted to be mounted to conventional cannulas of differing structures, material, and lengths. The ability of diameter reduction assembly 200 to detach from valve assembly 300 facilitates specimen removal through cannula 50 and reduces the profile of cannula 50 when diameter reduction assembly 200 is not needed at a particular point of the surgical procedure. It is envisioned that assembly 200 can also be configured to adapt to a variety of valve assemblies.

Figure 2:
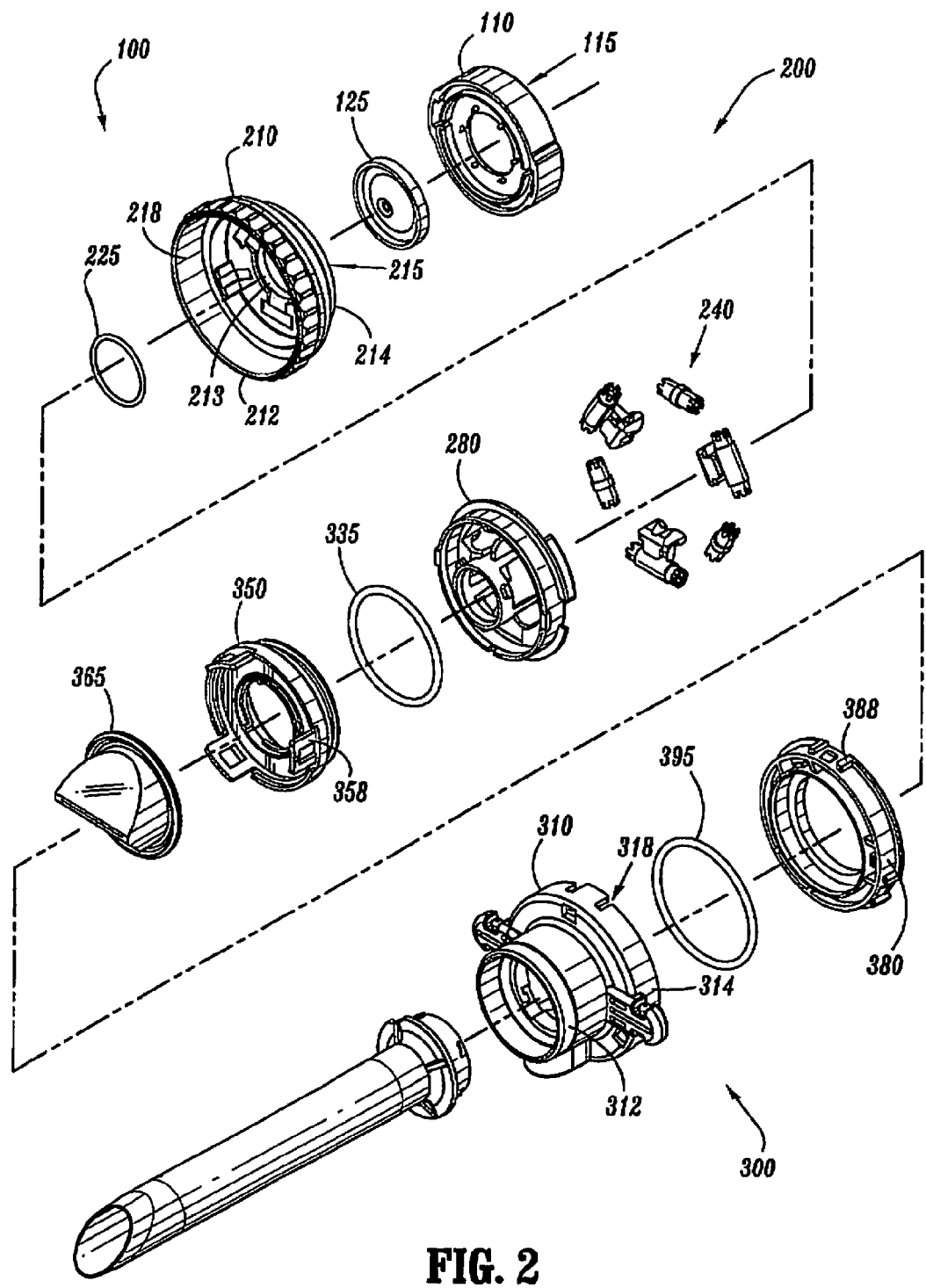
FIG. 2 is an exploded perspective view of the valve assembly and diameter reduction structure of FIG. 1.
Figure 3:
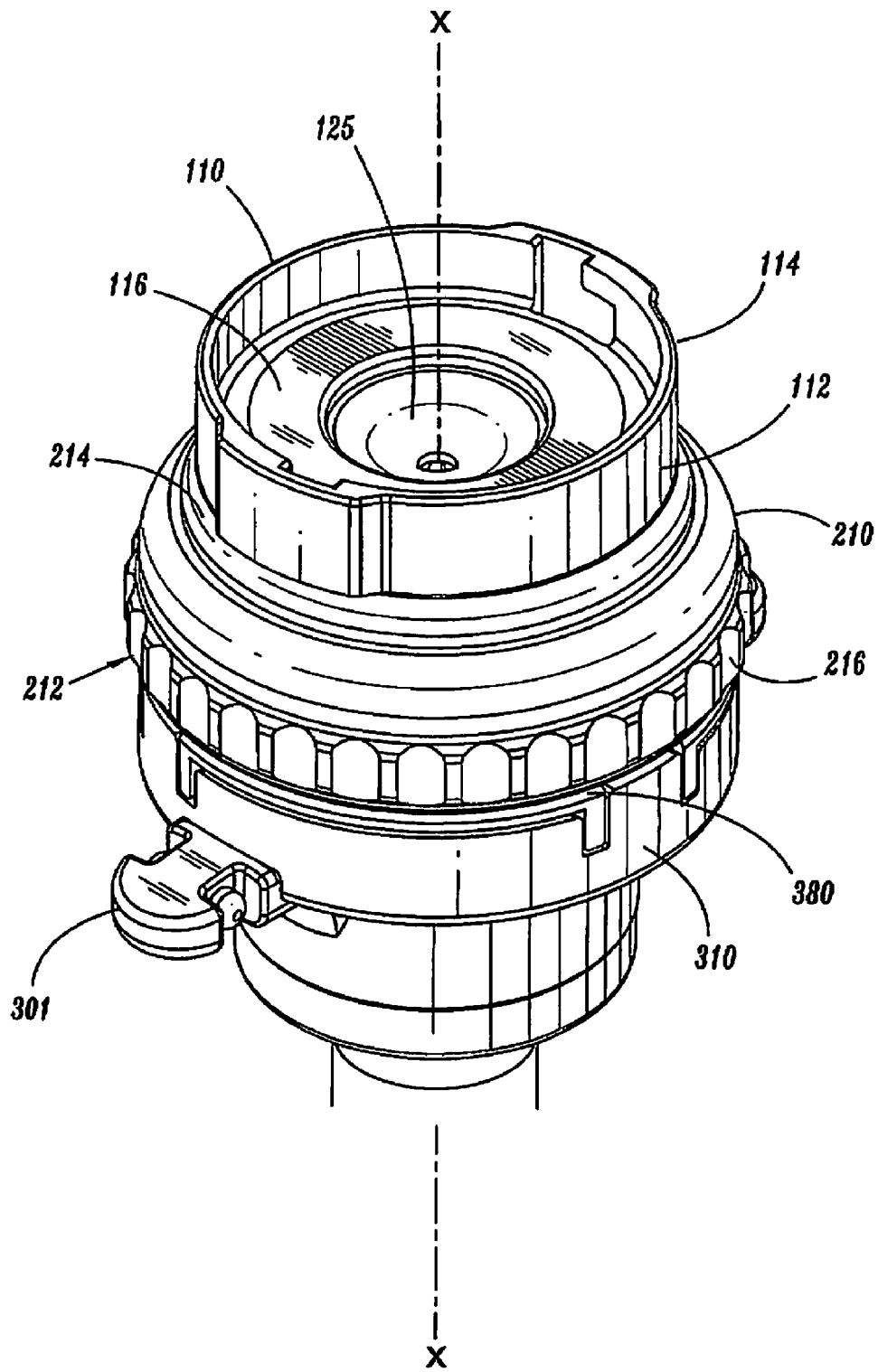
FIG. 3 is a close-up perspective view of a proximal end portion of the valve assembly and diameter reduction structure of FIG. 1.

Referring now to FIGS. 2-3, one preferred embodiment of the novel valve assembly and diameter reduction structure 100 of the present disclosure will be discussed in detail. Diameter reduction assembly 200 includes an end cap 110, a first seal 125, diameter reduction structure housing or first housing 210, a first O-ring 225, a diameter reduction structure 240, and a diameter reduction structure foundation element 280. Diameter reduction structure foundation 280 is connected with valve assembly 300 and defines a seal housing configured to be removably connected to cannula 50.

End cap 110 is generally tubular in shape and includes a distal end portion 112 and a proximal end portion 114. An annular shaped disc 116 defines a hole 115 aligned with the central longitudinal axis. End cap 110 is removably connected with diameter reduction structure housing 210.

First seal 125 is sealingly positioned between a distal side of the annular shaped disc 116 of end cap 110 and a proximal end portion of diameter reduction structure housing 210. First seal 125 forms a first exterior seal of assembly 100 and may be any conventional type of seal such as, but not limited to, a fixed or floating seal.

Diameter reduction structure housing 210 has a generally hemispherical shell shape decreasing in circumference from a distal end portion 212 to a proximal end portion 214. Correspondingly, distal end portion 212 defines a hole 215 having a diameter larger than the diameter defined by annular portion 213 of proximal end portion 214. Hole 215 is concentrically aligned with the central longitudinal axis-X. Proximal end portion 214 is configured to be connectively received by distal end portion 112. Distal end 212 includes an outside cylindrical portion 216 having a scalloped surface to facilitate handling thereof. A first O-ring 225 is seated on the inside surface of diameter reduction structure housing 210 in the vicinity of annular portion 213.

Figure 4:
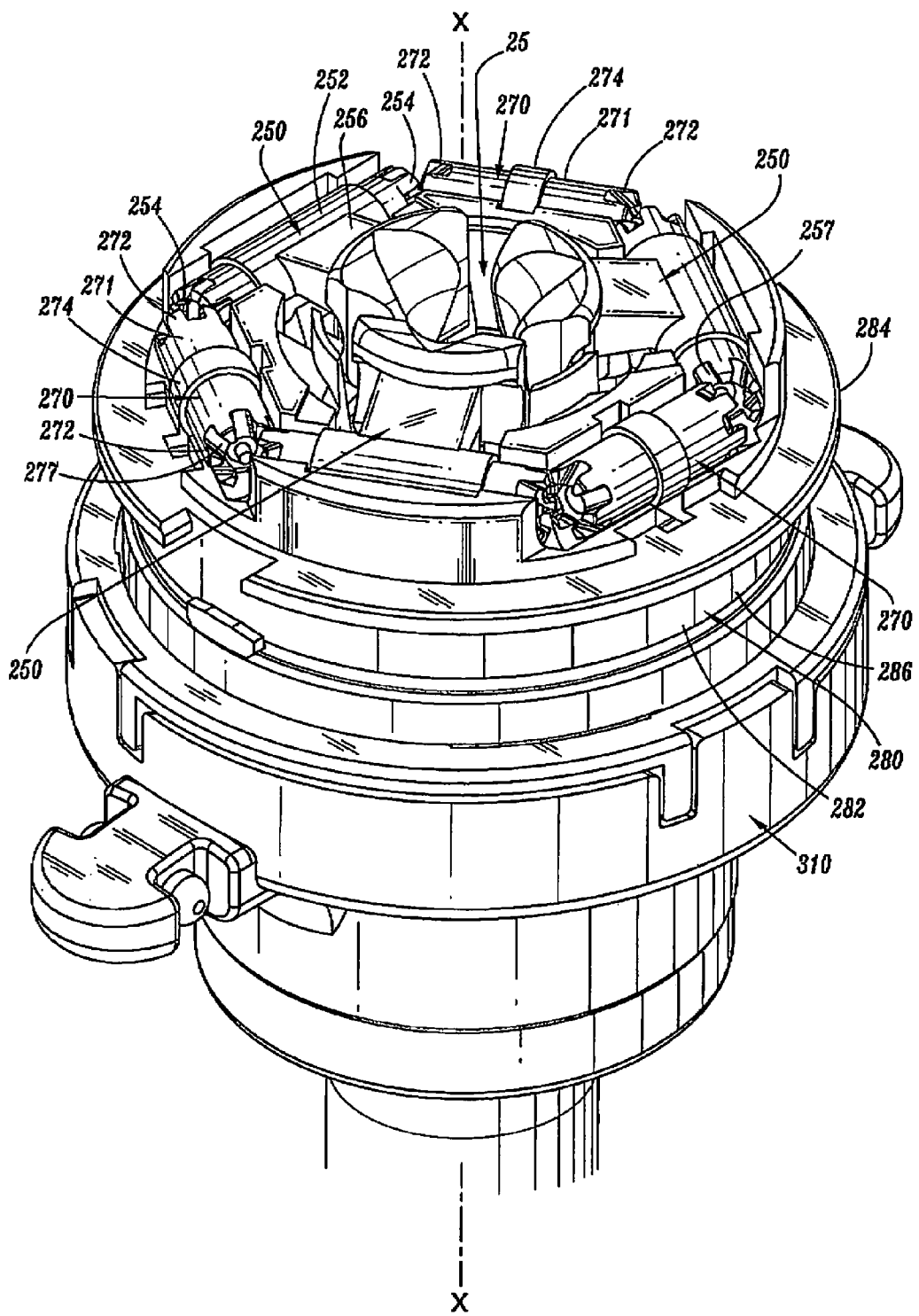
FIG. 4 is a close-up perspective view of the valve assembly and diameter reduction structure of FIG. 3 partially disassembled showing a diameter reduction structure positioned in a diameter reduction structure foundation element.

Referring now to FIGS. 2 and 4, diameter reduction structure foundation element 280 is configured to seat diameter reduction structure 240 on its proximal end portion 284 and support the movement of the diameter reduction structure 240 through a predefined range of motion and, in cooperation with housing 210, provides a suitable support structure for stand offs 250 when limiting the operational diameter of the passageway 25 through valve assembly and diameter reduction structure 100. Foundation element 280 has an outside cylindrical surface 286 and further defines a distally positioned generally tubular shaped portion 285 centered on the longitudinal axis.

Diameter reduction structure 240 includes a stand off assembly 245 having three stand off members 250 interconnected by a linking mechanism 270 having three linking members 271 in this one preferred embodiment. Stand offs 250 provide a predetermined degree of control over the movements of an instrument positioned within assembly 100. Linking mechanism 270 integrates and synchronizes the movement of stand offs 250.

Each linking member 271 is connected with and positioned between two adjoining stand offs 250 such that diameter reduction structure 240 forms an approximately hexagonal configuration of alternating stand offs 250 and linking members 271 centered around longitudinal axis X.

Each stand off member 250 includes a cylindrical cogwheel portion 252 defining a longitudinal axis-Y (see FIG. 8) and having opposing cylindrical end portions 254 with gears having cogs or teeth 255 extending parallel to longitudinal axis-Y. Linking members 271 also have a cylindrical shape defining a longitudinal axis-Z (see FIG. 6) and opposing ends 274 with gears having cogs or teeth 275. Teeth 275 extend parallel with the longitudinal axis-Z. Linking members 271 and stand off members 250 are positioned in diameter reduction structure foundation element 280 such that each respective cog 275 or 255 is configured, dimensioned, and positioned with suitable angular orientation to fit into a corresponding beveled slot 257 or 277, respectively, of the adjoining interrelated portion of diameter reduction structure 240 to integrate and coordinate the simultaneous movement of each stand off 250.

Linking members 271 provide a synchronizing function for the pivotal movement of stand offs 250 throughout their range of movement, wherein the diameter reduction structure 240 is at least partially repositioned to accommodate a larger diameter surgical instrument. The limitations of movement of the diameter reduction structure 240 in the second position include factors such as the diameter of the cannula, shape of the stand off, and internal portions of the trocar that limit the pivotal or rotational type travel of stand offs 250 away from the longitudinal axis. The second position is defined as when stand offs 250 are pivoted, flexed, or rotated in their seated position in diameter reduction structure 280 in a generally arcuate path distally and away from the longitudinal axis to increase the passageway 25 diameter defined by the interrupted annular barrier of diameter reduction structure 240.

Diameter reduction structure housing 210 and diameter reduction structure foundation element 280 are configured to support the positioning, diameter control function, and movement of diameter reduction structure 240. Housing 210 and foundation element 280 may be adapted to interface with a variety of different end caps, first seals, and seal housings, for example, as well as varying cannula sizes.

Figure 5:
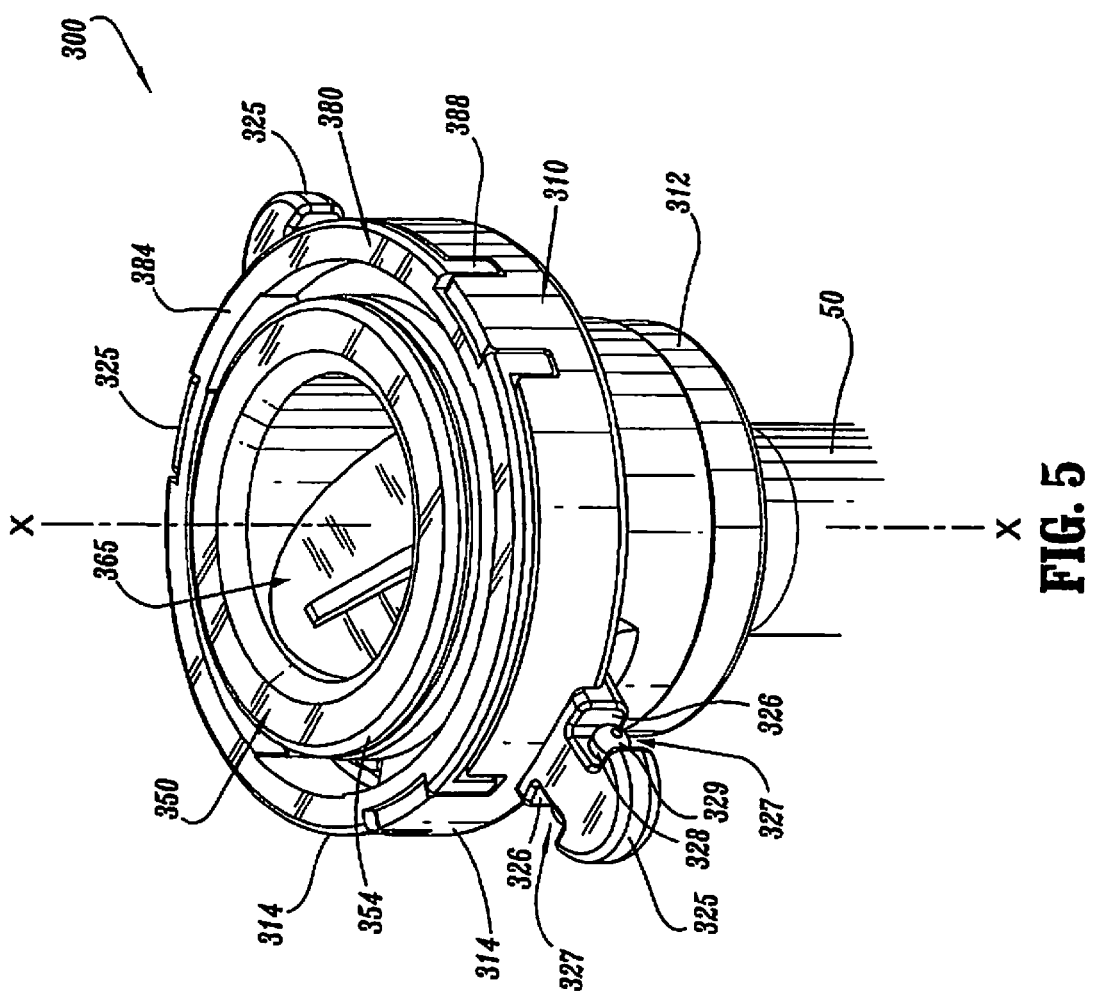
FIG. 5 is a close-up perspective view of the valve assembly and diameter reduction structure of FIG. 1 partially disassembled showing, a second seal.

Referring now to FIGS. 2 and 5, valve assembly 300 includes a second O-ring 335, a first seal support member 350, a second seal 365, a second seal support member 380, a third O-ring 395, and a seal housing or second housing 310 configured for connecting to cannula 50. Diameter reduction structure foundation 280 provides seating for second O-ring 335 providing a seal between distal end 282 and a proximal end portion 354 of first seal support element 350.

A second seal 365 includes a flange 367 for being sealingly positioned between a distal end portion 352 of first seal support element 350 and a proximal end portion 384 of second seal support element 380. First seal support element 350 is generally annular in shape with an outside cylindrical surface 356 and has three distally extending tabs 358. A second seal support element 380 also has a generally annular shape with an outside cylindrical surface 386 and is configured with radially extending tabs 388. A third O-ring 395 provides a seal between second seal support element 380 and seal housing 310.

Seal housing 310 has a proximal end portion 314 including radially aligned slots 318 configured to correspondingly mate with tabs 388 and a distal end portion 312 configured to mate with cannula 50 utilizing a suitable attachment mechanism such as a bayonet or threaded connection.

Seal housing 310 further includes two diametrically opposed cantilevered portions 325. Each cantilevered portion includes two opposed notches 326 having suture attachment fixtures 327 generally perpendicular to portions 325. Attachment fixtures 327 include a cylindrical portion 328 and a hemispherical portion 329 configured for an easy tie off of sutures for the positive retention of the trocar assembly in position within the patient against the sufflation pressure typically employed in minimally invasive surgery.

Second seal 365 is shown as a duck bill type seal, but it may be any seal system such as a frusto-conical seal, for example, that may be adapted to perform the function of a second seal. Second seal support element 380 is positioned in seal housing 310.

End cap 110, diameter reduction structure housing 210, diameter reduction structure foundation element 280, first seal support element 350, second seal support element 380, and seal housing 310 are preferably made of a medical grade plastic, metal, or composite materials having suitable strength and resilience for its application. In one preferred embodiment, the above assemblies are injection molded using a medical grade plastic. The O-rings are made of a medical grade plastic or rubber suitable for providing a fluid tight seal between generally rigid structural members.

Referring now to FIGS. 6-8, in one preferred embodiment, linking member 271 is shown aligned with longitudinal axis-Z. A band 272 having an increased circumference and predetermined width is positioned on the cylindrical surface 274 of each linking mechanism 270. Cogs 275 have a first arcuate width congruent at the outside surface of cylindrical portion 274 that tapers or bevels to a narrower second arcuate width at the opposing side of each cog 275. Thus, cogs 275 extend inwardly from surface 274 to a predetermined point between surface 274 and longitudinal axis-Z. Cogs 275 extend beyond and at least partially surround a recessed flat portion 278 that may include at least one pin 279. Pin 279 is concentric with longitudinal axis-Z and extends axially. Slots 277 are defined by cogs or teeth 275 and beveled portions of cylindrical portion 274.

Diameter reduction structure foundation element 280 is shown with distal end portion 282 connecting with tubular shaped portion 285 and proximal end 284. Tubular shaped portion 285 is positioned to guide instruments being inserted into the second seal and has an inside diameter at least approximately equal to the diameter of passageway 25. Radially extending tabs 287 and 289 positioned on tubular shaped portion 285 and cylindrical portion 286, respectively, are configured and dimensioned to sealingly engage first seal support element 350 with foundation element 280 in combination with O-ring 335. Cylindrical portion 286 has an annular shape including a radially extending lip 281. Proximally extending tabs 288 and at least partially concave cavities 290 are configured to support the rotation or flexing of diameter reduction structure 240 within proximal end portion 284.

Stand off members 250 have a head 260 connected by an arm 256 to a base portion 251 with opposing cylindrical end portions 254 aligned with a longitudinal axis-Y. A tubular band 252 has a circumference greater than the circumference of end portion 254. A longitudinally aligned notch 252a is formed in band 252 near the base of arm 256. Cogs 255 have a first arcuate width congruent with the surface of cylindrical portion 254 that tapers to a narrower second arcuate width at the opposing side of each cog 255. Thus, cogs 255 extend inwardly from surface 254 to a predetermined point between surface 254 and longitudinal axis-Y. Slots 257 are defined by cogs or teeth 255 and beveled portion of cylindrical end portion 254. Cogs 255 extend along axis-Y beyond and at least partially surround a recessed flat portion 258 that may include a pin 259. Pin 259 is concentric with longitudinal axis-Y and extends axially from portion 258. Head 260 has a generally hemispherical or bulbous shape having an exterior surface and a concave interior surface 266.

Head 260 includes a first side 262 having a generally planar face and an opposing tapered second side 268. First side 262 includes a cantilevered extension 261. A third side 264 includes a generally convex portion and beveled side portions 265. A fourth side 266, opposing, the third side 264, has a generally planar face that is connected with arm 256. Head 260 also includes a centrally positioned segmented concave notch 263 approximately perpendicular to longitudinal axis-Y. The generally concave shape of notch 263 is configured and dimensioned to accommodate a limited degree off axis movement by small surgical tools when diameter reduction structure 240 is in a first or initial position. Arm 256 connects head 260 with base portion 251.

Diameter reduction structure 240 components, including stand off assembly 245 and linking mechanism 270, are preferably fabricated from at least one medical grade plastic, laminates of medical grade plastics, or composite materials of suitable flexibility, bias, rigidity, and compressive strength for application as diameter reduction structure. Different materials may also be bonded together in this structure depending on the application, for example, head 260 may be fabricated from one medical grade plastic that is of greater resiliency than a second medical grade plastic that forms arms 256. Similarly, linking members 271 may be formed of similarly suitable one or more medical grade plastic or composite materials.

Further, the system of cogs synchronizing the movement of stand offs 250 and linking members 271 are but one type of linking mechanism 270 known by those skilled in the art suitable for synchronizing the movements of stand offs 250 and other suitable alternative mechanisms such as, but not limited to a pulley system, a flexible synchronizing shaft, or an articulated joint performing the same function are envisioned.

Figure 9:
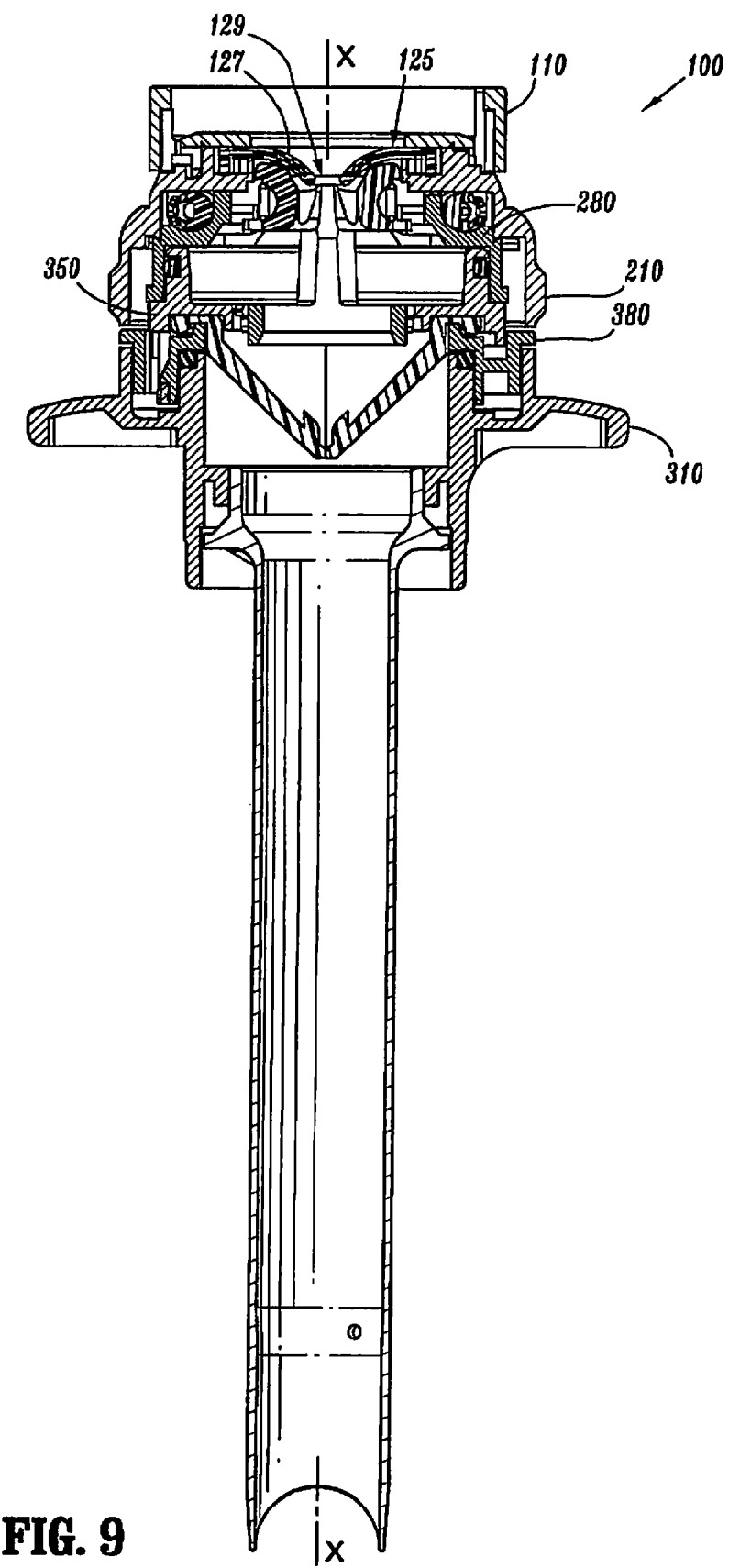
FIG. 9 is a cross-sectional view of the valve assembly and diameter reduction structure of FIG. 1 along lines 9-9.
Figure 10:
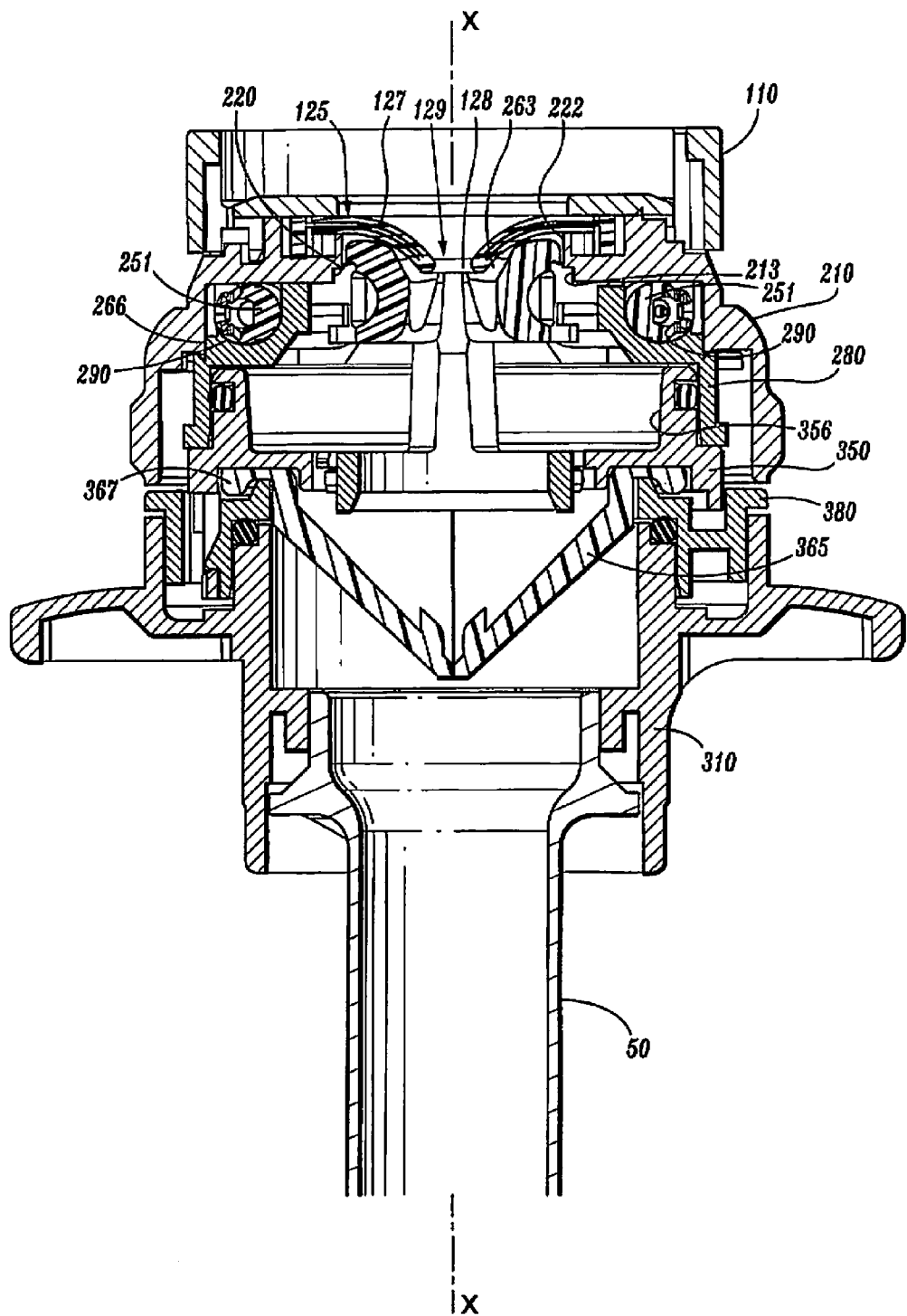
FIG. 10 is a close-up of the cross-sectional view of the valve assembly and diameter reduction structure of FIG. 9.

Referring now to FIGS. 9, and 10, valve assembly and diameter reduction structure 100 and cannula 50 are shown in cross-section. First seal 125 includes concave or arcuate membrane portion 127 that extends radially inwardly and distally forming a distal end portion 128 defining a hole 129. Portions 127 are in close proximity to or abut stand off members 250. Stand off members 250 are shown in a first position having an orientation generally perpendicular to central longitudinal axis-X. The depth and width of segmented notches 263 are shown relative to hole 129 and second side 264 and provide a limited and increased degree of off axis movement or angular movement of small surgical instruments.

Stand offs 250 include a base portion 251 positioned in proximity to or abutting cantilevered portion 218. Cantilevered portion 220 includes wall 222 configured to act as a stop to limit the radially outward movement of heads 260 of stand off members 250. The material of construction of stand off members, and especially head 260, may be selectively controlled to provide a range of flexibly compressive bias against parallel off axis and angular movements or surgical instruments.

Diameter reduction structure housing 210 at least partially encloses diameter reduction structure foundation element 280 and first seal support element 350. Flange 367 of second seal 365 is secured between first seal support element 350 and second seal support element 380. Seal housing 310 at least partially encloses second seal support element 380. Cannula 50 connects with distal end portion 312 of seal housing 310.

Figure 11:
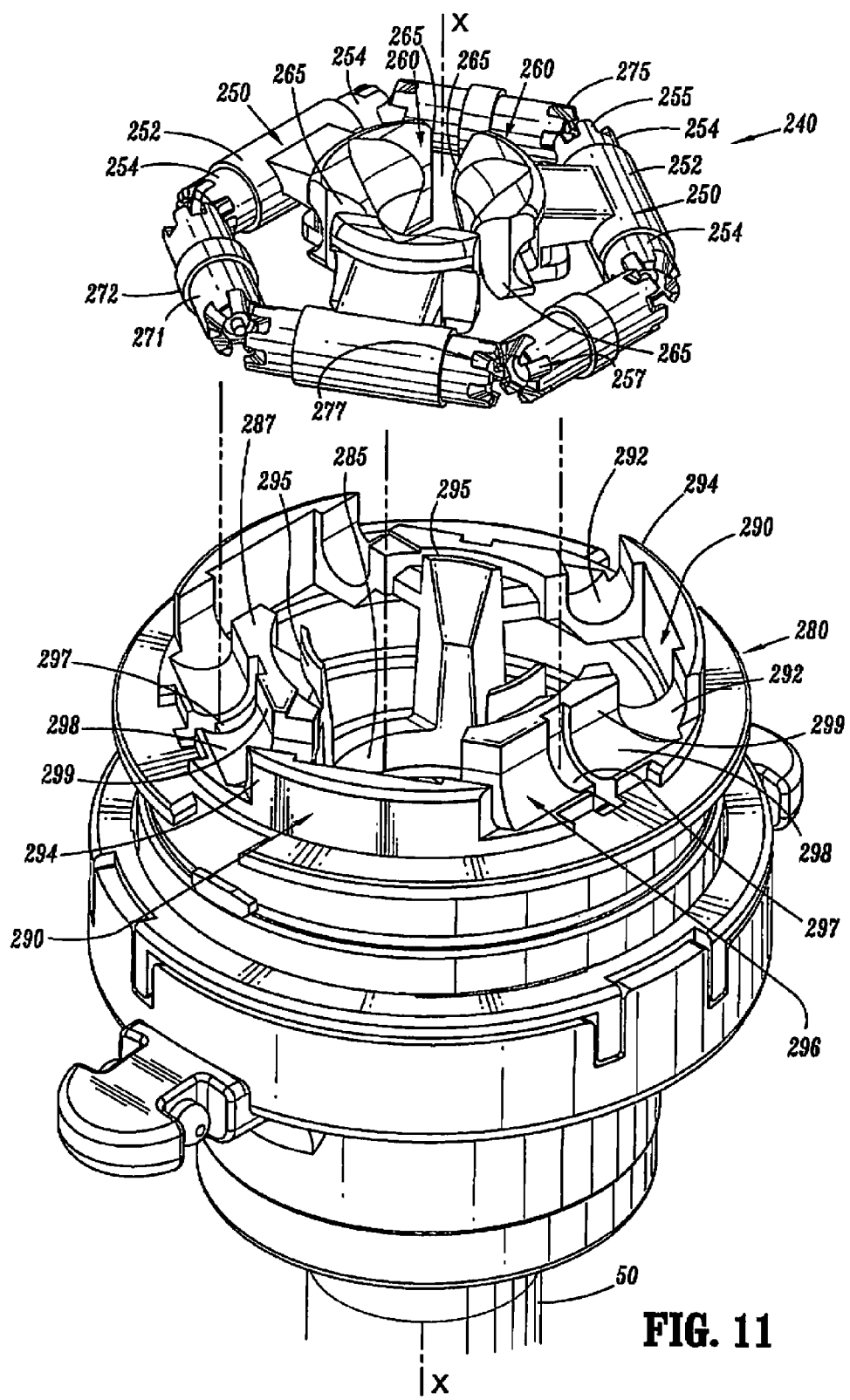
FIG. 11 is an exploded view of the diameter reduction structure and the diameter reduction structure foundation element of FIG. 4.

In FIG. 11, diameter reduction structure 240, shown as an integrated assembly in the first position, for placement within diameter reduction structure foundation element 280. Foundation element 280 is configured to provide suitable positioning for diameter reduction structure 240 to control the operable diameter and thus improving the ability of the sealing system of assembly 100 to retain its integrity during procedures utilizing small instruments. This includes a suitable supporting structure for stand offs 250 to act as a barrier providing a controlled limitation to the movement of surgical instruments and supporting the movement of diameter reduction structure 240 between the first and second positions.

The first position of structure 240 being defined by heads 260 forming an interrupted annular barrier structure suitable for controlling forces in a plane generally orthogonal to the longitudinal axis-X resulting from parallel off axis and angular movements or movements generally orthogonal to the longitudinal axis of small surgical instruments positioned in passageway 25. The third sides 264 of heads 260 defining the second operable area in the first position.

In the first position, beveled portions 265 of heads 260 define gaps or interruptions in the annular barrier structure formed by diameter reduction structure 240. The size of the gap is controlled by the shape and position of heads 260 and is configured to ensure smaller diameter surgical instruments are precluded from passing between heads 260. Diameter reduction structure 240 further includes a controlled bias configured to resist the movement of reduction structure 240 radially in an outward direction as well as from the first position to the second position. The bias in structure 240 also serves to return structure 240 to the first position after the removal of the larger diameter surgical instrument.

The second position being defined by diameter reduction structure 240 moving at least partially distally to accommodate the unrestricted passage or of individual larger sized diameter surgical instruments through diameter reduction structure 240 and cannula 50.

Foundation element 280 includes at least partially concave seating positions 296 for linking members 271 and 290 for stand off members 250. Seating positions 290 define an interrupted channel having two distinct seats or supports 292 configured and dimensioned to receive cylindrical end portions 254. Band 252 is positioned between supports 292. Seating positions 290 further include an arcuate support member 294 with a proximally extending straight portion 299.

Seating positions 296 define an at least partially concave channel portions 298 separated by a slot or recess 297 configured and dimensioned to receive surface 274 and band 272 of linking member 271. Seating positions 296 include a proximally extending straight portion 299.

Seating positions 290 and 296 are structurally supported by a proximally extending member 295. Member 295 is connected by arms to portions 292 and 298 and is configured to structurally support portions 292 and 298 from excessive deflection or movement.

Seating positions 290 and 296 provide the alignment; spacing, and angular orientation critical for the interrelation of cogs 255 and 275 with their respective slots 277 and 257 for the synchronizing of the movements of stand offs 250 and linking members 271. In addition, diameter reduction structure 240 includes a bias to the first position as individual components or as an assembly either as a result of its positioning within diameter reduction structure foundation element 280, a separate bias member such as an elastic band, or by combinations thereof. When fully assembled with diameter reduction structure housing 210 (see FIG. 2) and diameter reduction structure foundation 280, diameter reduction structure 240 is capable of performing its functions at any angle or in any direction of use without any operator action.

Figure 12:
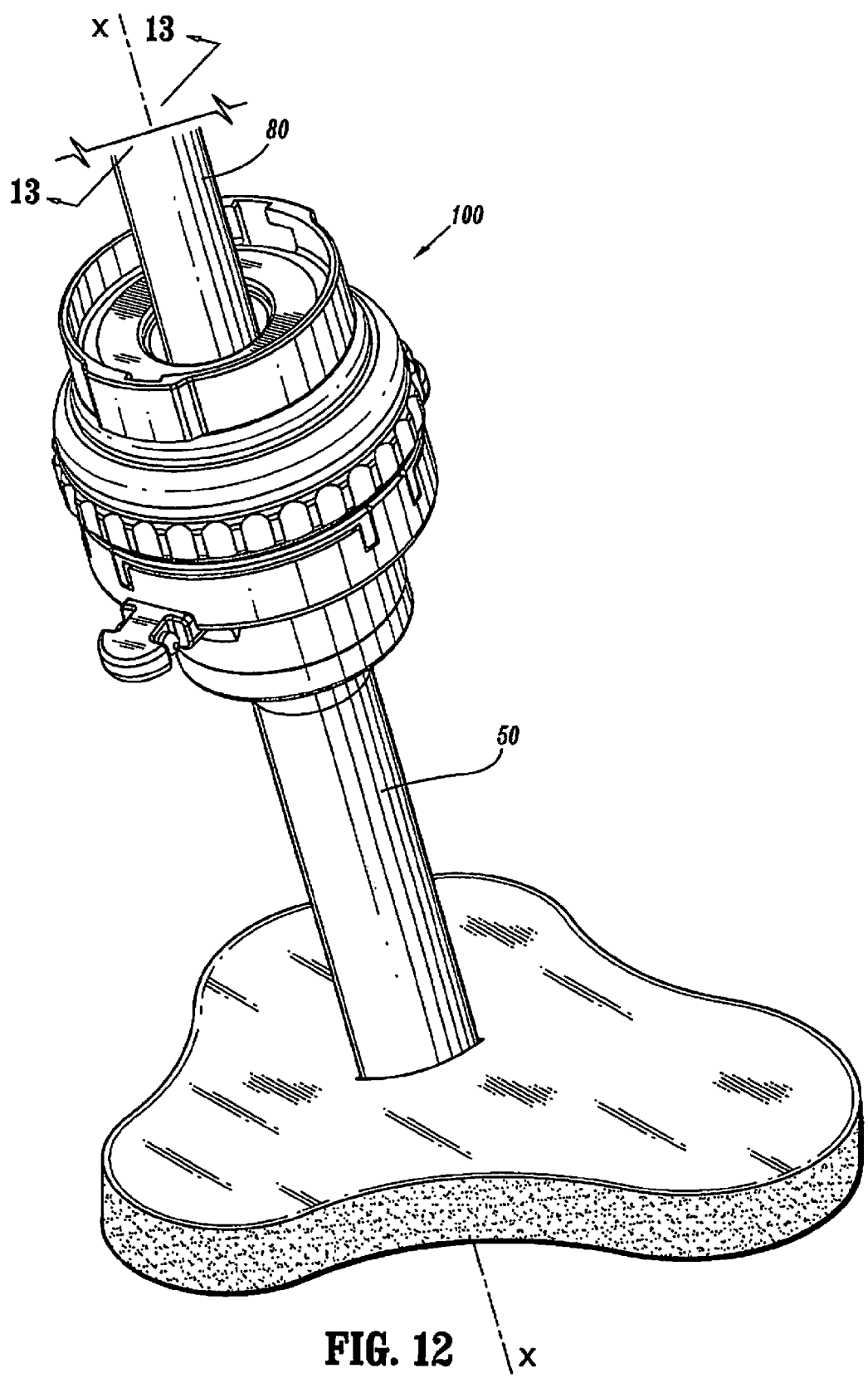
FIG. 12 is a perspective view of the valve assembly and diameter reduction structure of FIG. 1 being operationally employed with a large diameter surgical instrument passing through the valve assembly and diameter reduction structure and into a tissue portion of a patient.
Figure 13:
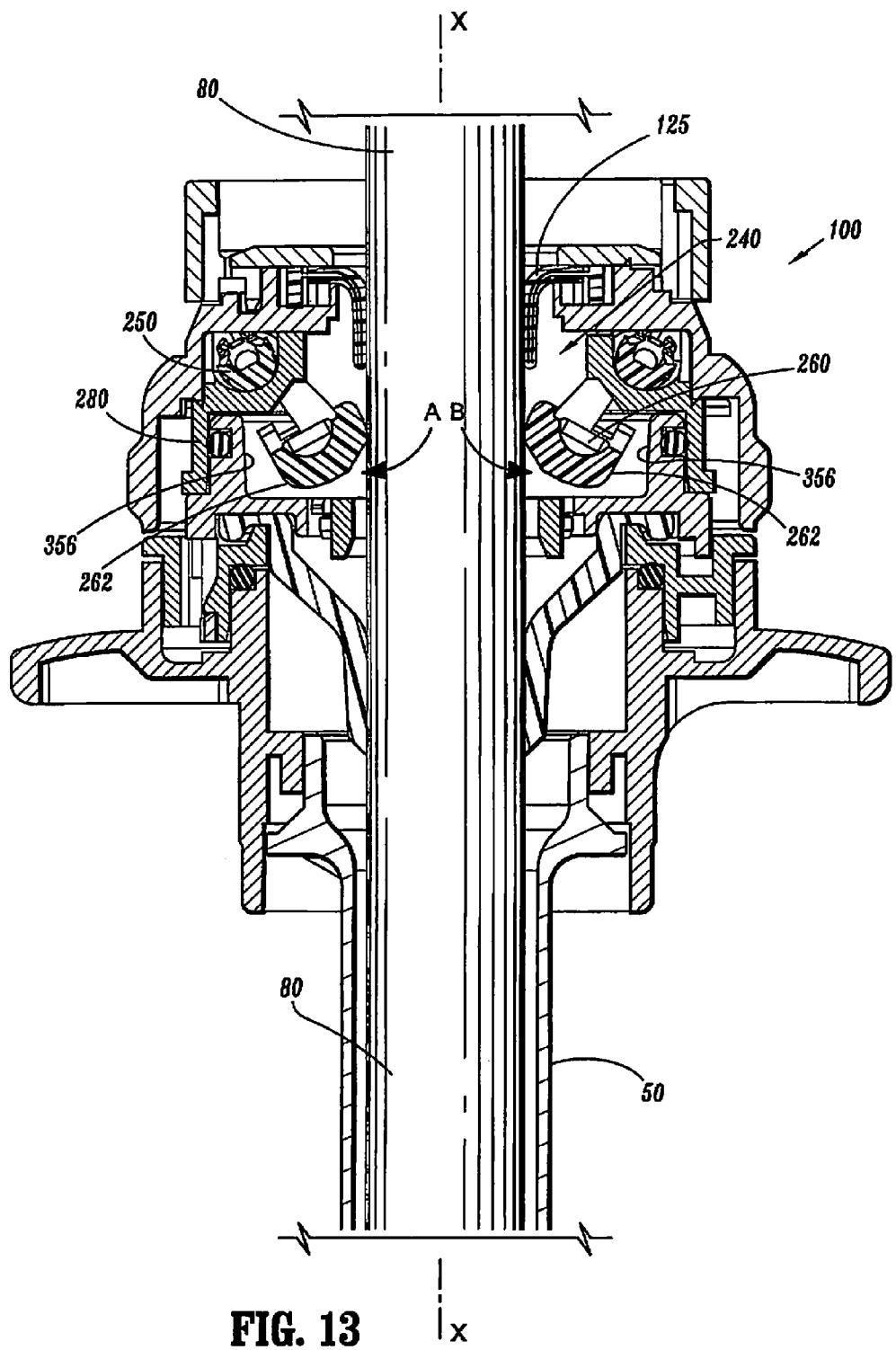
FIG. 13 is a close-up of the cross-sectional view of FIG. 12 along lines 13-13 showing the repositioning of the diameter reduction structure for the large diameter surgical instrument.

Referring now to FIGS. 12 and 13, diameter reduction structure 100 is shown in an operational position. A large diameter medical instrument 80 defining a second longitudinal axis is positioned through valve assembly and diameter reduction structure 100 and cannula 50. A large diameter surgical instrument is an instrument having a diameter or an cross-sectional area orthogonal to the second longitudinal axis less than a first diameter or first operable area of passageway 25, but greater than the second diameter or second operable orthogonal to the central longitudinal axis defined by the stand off assembly in the first position. Similarly, a small diameter surgical instrument 60 defining a first longitudinal axis has a diameter or cross-sectional area orthogonal to the first longitudinal axis less than the second diameter or second operable defined by the stand off assembly in the first position. Thus, the large instruments by definition being larger than the second operable area must at least partially deflect stand off assembly 240 distally in order to enter the passageway. In contrast, the small instruments can be positioned axially within the second operable area without deflecting stand off assembly 240. In this one preferred embodiment, large instruments are those defined as having diameters greater than 5.5 mm and small instruments those defining diameters equal to or less than 5.5 mm. The 5.5 mm distinction between large and small instruments is relative to the diameter of the passageway defined in the trocar and can vary depending upon the diameter of the trocar apparatus the valve assembly and diameter reduction structure 100. When large diameter instrument 80 is moved distally along central longitudinal axis-X through first seal 125 and into contact with diameter reduction structure 240, the axially aligned force component moving large diameter instrument 80 has to overcome the bias configured to retain diameter reduction structure 240 in the first position, as shown in FIG. 10.

As the force behind instrument 80 exceeds the bias configured to maintain diameter reduction structure 240 in the first position, diameter reduction structure 240, pivots or rotates in a generally arcuate movement in a generally distal direction initially and then continues its pivotal or rotational arcuate movement, as shown by arrows "A" and "B", away from the central longitudinal axis to define the third operable area and accommodate the passage of large diameter instrument 80. The amount of bias employed to retain diameter reduction structure 240 in the first position is controlled by factors such as the materials of construction of diameter reduction structure 240 as well as the methods employed of securing diameter reduction structure 240 in position in diameter reduction structure foundation element 280.

When forced towards the inside diameter of wall 356 by the shaft of large diameter of instrument 80, stand offs 250 move to a second position wherein face 262 of head 260 is placed approximately parallel with and in apposition to wall 356. The spatial relationship between wall 356 and diameter reduction structure 240 in the second position is a function of individual trocar interior configurations, the inside circumference of passageway 25, and the intended application of the valve assembly and diameter reduction structure 100. Valve assembly and diameter reduction structure 100 is configured to provide suitable space for the pivoting or flexing of diameter reduction structure 240 and still accommodate larger diameter instruments 80 that conform with the maximum inside diameter for a given cannula 50. Upon withdrawal of larger diameter instrument 80, diameter reduction structure 240 is biased to reposition to a first position wherein a portion of each stand off 250 is adjacent wall 220.

Figure 14:
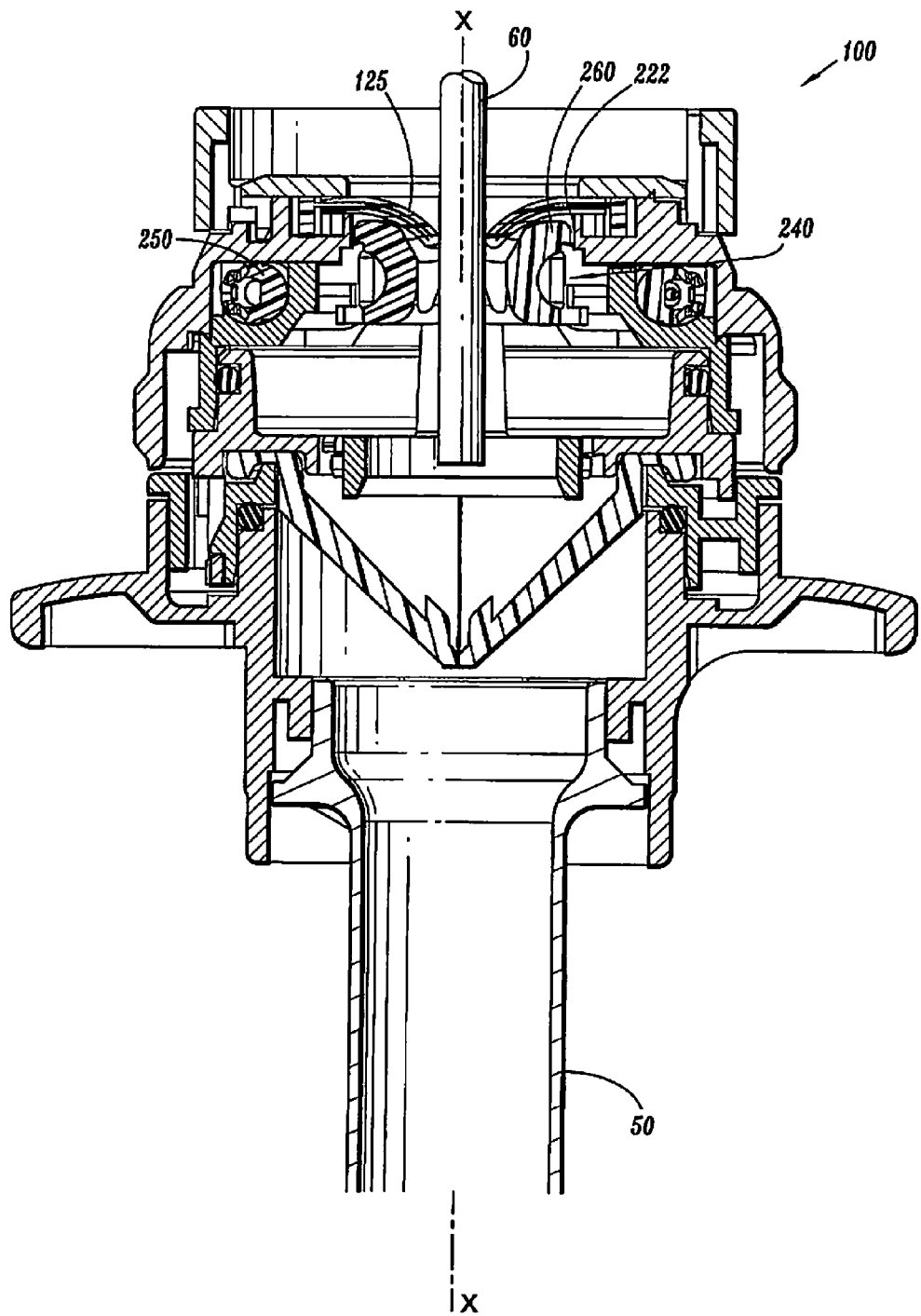
FIG. 14 is a close-up cross sectional view of the valve assembly and diameter reduction structure of FIG. 10 showing a small diameter surgical instrument being positioned at least partially therein.
Figure 15:
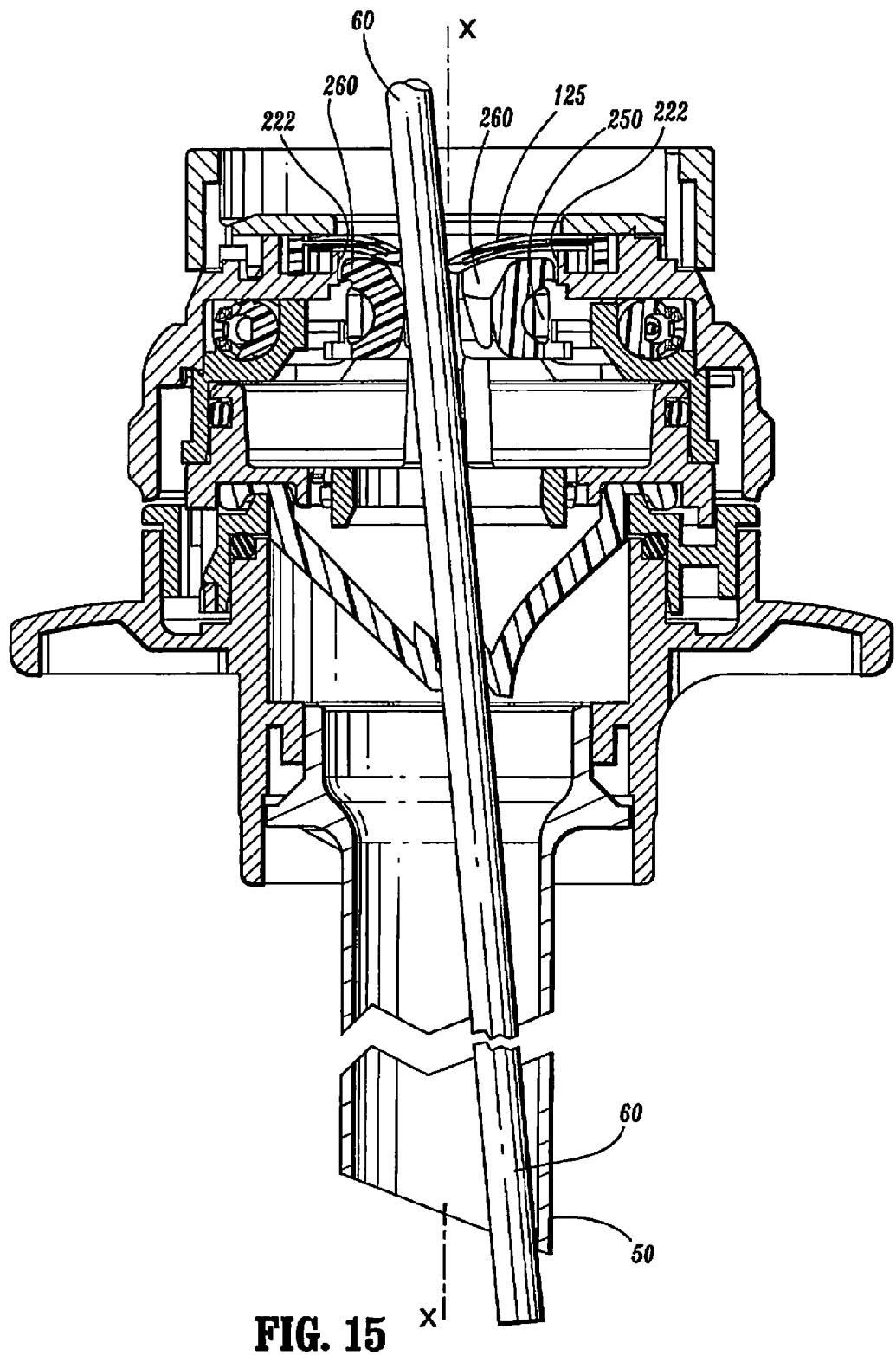
FIG. 15 is the cross-sectional view of FIG. 14 showing the diameter reduction structure controlling the angular movement of a small diameter surgical instrument positioned therein.
Figure 18A:
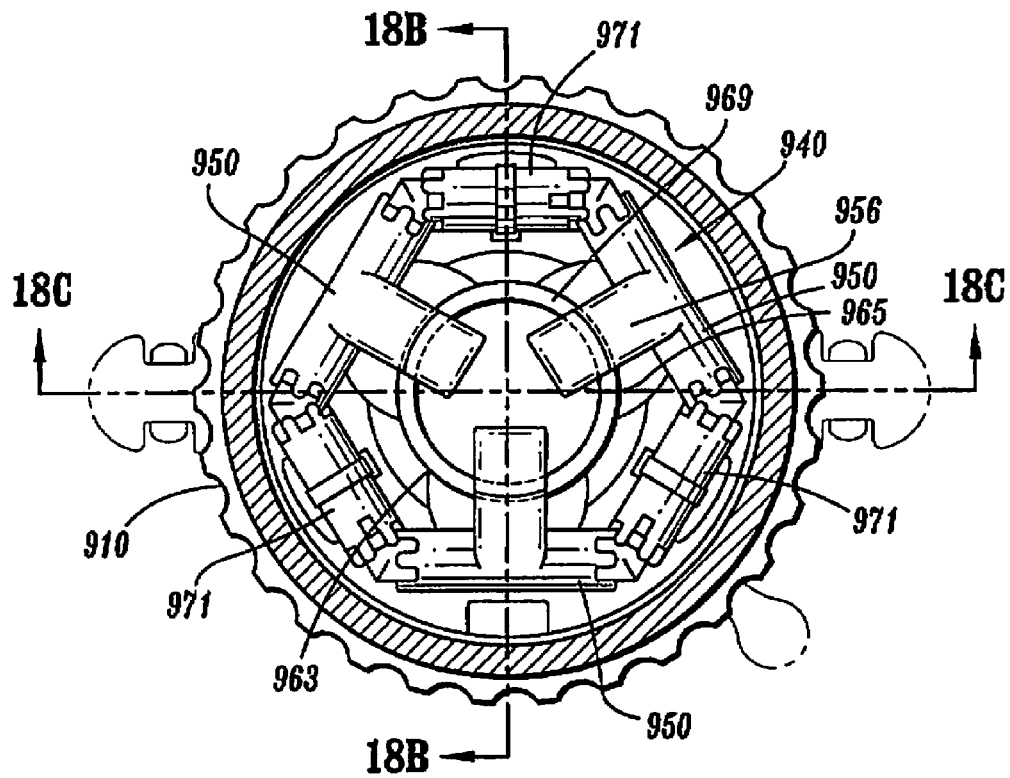
FIG. 18A is across-sectional view of the trocar illustrating the diameter reduction structure of FIG. 17 along line 18A-18A.
Figure 18B:
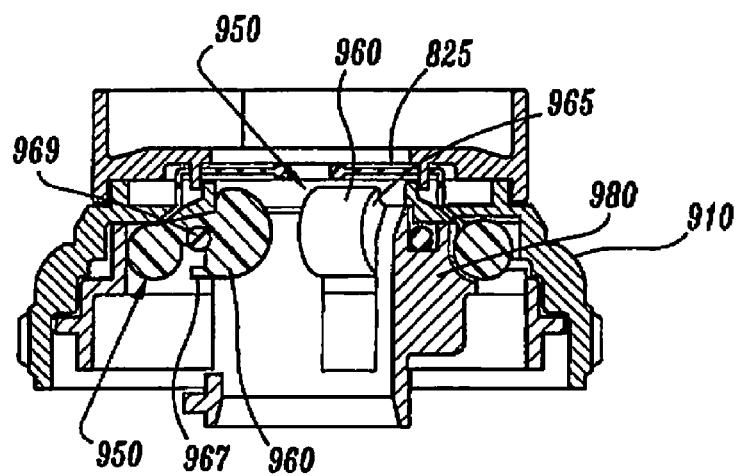
FIG. 18B is a cross-sectional view of the valve assembly and diameter reduction structure of FIG. 18A along line 18B-18B.
Figure 18C:
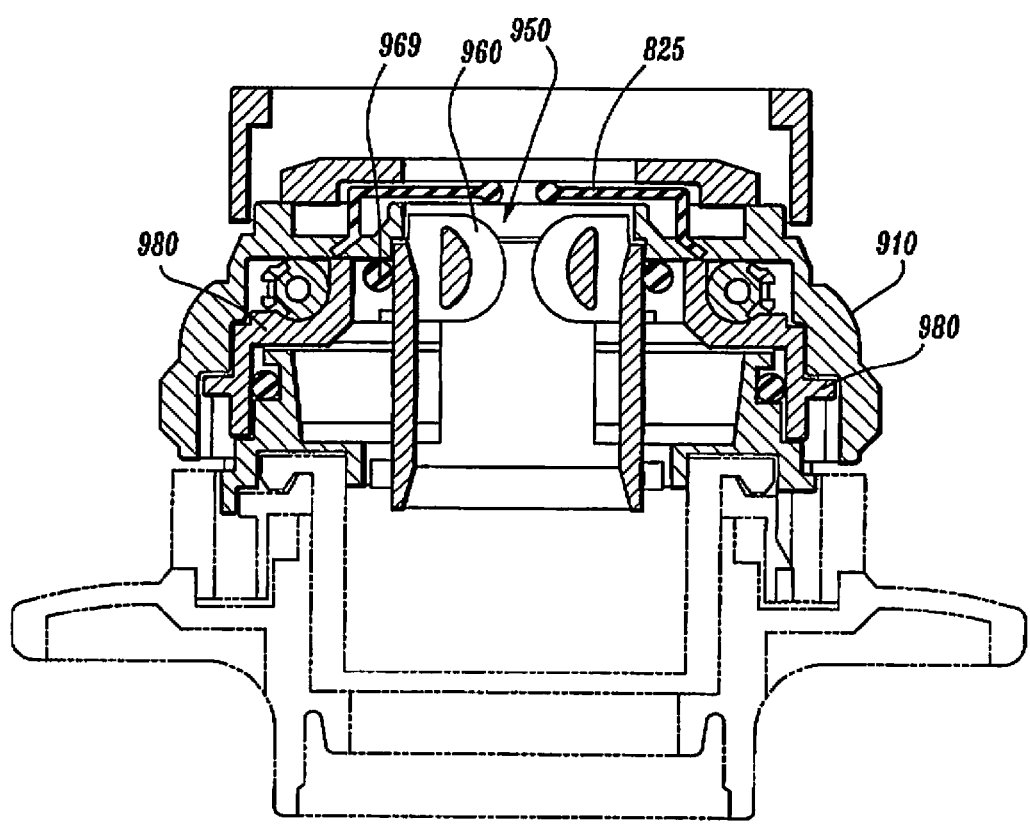
FIG. 18C is a cross-sectional view of the valve assembly and diameter reduction structure of FIG. 18A along line 18C-18C.

Referring now to FIGS. 14 and 15, stand off members 250 are shown in a first or diameter reduction position, wherein head 260 extends in a generally radial direction relative to longitudinal axis-X. Cantilevered portion 222 provides a generally rigid barrier configured to structurally support and limit the radial displacement of head 260. Diameter reduction structure 240 in the first position is configured to accommodate the penetration of smaller diameter instruments 60 through valve assembly and diameter reduction structure 100 and into cannula 50 without any movement.

When in this first position, stand off member 250 is placed at least partially in axial compression by a force with a component perpendicular to central longitudinal axis-X as a result of the orthogonal or angular movements of a small diameter surgical instrument 60. Each stand off member 250 is mounted in diameter reduction assembly 200 to provide a limit to excessive parallel off axis and angular movements of small diameter surgical instruments 60.

A small diameter surgical instrument 60 is positioned through seal 125 and into cannula 50 typically with little or no substantial contact with diameter reduction structure 240. When small diameter surgical instruments 60 are manipulated to make off axis or angular movements, however, small diameter surgical instruments 60 come in contact with at least one head portion 260 and the inside circumference of cannula 50 which act in combination as two separate and approximately parallel structural barriers to control outwardly directed off axis and angular movements away from central longitudinal axis-X. The combination of head 260 and cantilevered portion 222 may be configured as a rigid or flexible biased structure. This controlling mechanism functions to bound the operational movements by small diameter surgical instruments 60, sufficiently to retain the integrity of the sealing system.

Referring now to FIGS. 16A, 16B, and 16C, in another preferred embodiment, valve assembly and diameter reduction structure 500 includes a proximal end portion or diameter reduction assembly 600 and a valve assembly 700 similar to the previous embodiment, however, diameter reduction structure 640 is positioned proximal to a first seal 525.

Diameter reduction structure 500 includes an end cap 510, a diameter reduction structure housing 610, a diameter reduction structure 640, a diameter reduction structure foundation element 680, and as required a first O-ring.

End cap 510 has a generally cylindrical shape including a distal end portion 512 and a proximal end portion 514. Proximal end portion 514 includes an annular shaped disc or portion 516 defining a hole 515 aligned with the central longitudinal axis-X. In this configuration, annular portion 516 may be a rigid plastic or a flexible membrane not configured to be a seal. Thus, hole 515 could be configured as a rigid or flexible barrier and having a diameter at least equal to the inside diameter of a cannula 50 in a rigid configuration.

Diameter reduction structure housing 610 has a generally hemispherical shell shape decreasing in circumference from a distal end portion 612 to a proximal end portion 614. Proximal end portion 614 includes an annular portion 613 defining hole 615. Hole 615 preferably has a larger diameter than hole 515. Proximal end portion 614 is configured to be connectively received by distal end portion 512. Distal end portion 612 includes an outside cylindrical portion 616 having a scalloped surface to facilitate handling thereof.

Diameter reduction structure 640 includes a stand off assembly having three stand off members 650 and a linking mechanism 670 is positioned proximal to a first seal 525. Stand offs 650 provide a predetermined degree of control over and limitation to the movements of instruments positioned within assembly 600. Linking mechanism 670, in the form of three linking members 671, integrate and synchronize the movement of stand offs 650. While the specific configuration of stand off members 650 or linking mechanism 670 may vary, stand off assembly 645 is employed operationally as described in all of the embodiments herein to limit the off-axis and angular movements of small surgical instruments.

Diameter reduction structure foundation element 680 is configured to seat diameter reduction structure 640 on its proximal end portion 682 and includes at least partially cantilevered seating positions 690 configured to support and control the movement of reduction structure 640 throughout a predefined range of motion as at least partially represented by arrow "A". A distally extending tubular portion 685 is configured for the positioning of first seal 525. First seal 525 is positioned approximately orthogonal to longitudinal axis-X and may be a fixed or—a floating type seal.

A first seal support element 750 has a generally tubular shape with a distal end portion 754 abutting a proximal side of cantilevered seating portion 690 and a distal end 752. First support element 750 has an inside wall 756 that may be configured to limit the distal range of motion of stand offs 650. A cantilevered portion 753 of first seal element 750 is positioned to secure and seal a flange 767 of a second seal 765 in positioned between a proximal portion of second seal support element 780.

A distal end 752 of first support element 750 at least partially encloses and sealingly positions a flange 767 of second seal 765 in cooperation with a distal end portion 782 of a second seal support element 780. Second seal 765 may be any type of seal, but is preferably a duck bill type seal commonly configured for use with a fixed or floating first seal. In the preferred embodiment, second seal 765 is a duck bill type seal extending distally into a seal housing 710.

Seal housing 710 includes a proximal portion 714 configured to secure and at least partially enclose second seal 765 and at least a portion of second seal support element 780 and first seal support element 750. Second seal support element 780 also has a generally annular shape and is configured to lock with and engage first seal support element 750. Seal housing 710 has a distal end portion 712 configured to mate with a cannula.

Valve assembly and diameter reduction structure 500 is configured as an assembly for controlling the off axis and angular movements of small surgical instruments externally or proximally to the sealing system. This configuration reduces the strain placed on the first seal by further limiting the range of angular motion to which the first seal is subjected to by small surgical instrument manipulation and thereby improving the integrity of the trocar sealing system. In addition, while valve assembly and diameter reduction structure 500 may be removably connected to a correspondingly dimensioned cannula 50, it is also envisioned that end cap 510, housing 610, diameter reduction structure 640, and foundation element 680 may be readily adapted as an integrated assembly, for example, with or without an integrated first seal 525, for use with a wide range of trocar assemblies having fixed or floating seals to advantageously control off-axis and angular movements of small surgical instruments without interrupting the integrity of the sealed portions of the trocar.

Referring now to FIGS. 17 and 18A-18C, one of the preferred embodiments of a valve assembly and diameter reduction structure 800 includes a proximal end portion or diameter reduction assembly 900 and a distal end portion or valve assembly 1000. Diameter reduction structure 940 is positioned distal to a first seal 825 and within a diameter reduction structure housing 910.

Diameter reduction structure 940 is illustrated with a stand off assembly 945 having three stand offs 950 and three linking members 971 positioned in a diameter reduction structure foundation 980. While the general configuration of diameter reduction structure foundation 980 and linking members 971 are structurally and operationally similar to earlier embodiments, stand offs 950 have a different configuration head portion 960, similar to that depicted in FIG. 16A, with side portion 965 having a generally planar shape and a width approximately equivalent to arm 956.

Head portion 960 may also include an attachment mechanism 963 and a cantilevered extension or flange 967. Flange 967 extends radially from head 960 toward base 961 in the first position. In the second position of stand off 950, flange 967 can be configured with a suitable length to at least partially limit the range of movement of stand off 950 by contacting an inside wall of diameter reduction structure housing 910. Attachment mechanism 963 is configured to receive and retain an annularly shaped bias member 969 on stand off 950 throughout its range of motion. Annularly shaped biased member 969 is configured to bias stand offs 950 to the first position, provide an additional bias when off axis or angular movements act to compress a stand off 950 in a radially outward direction against the diameter reduction structure foundation 980 or housing 910, and act as an uninterrupted barrier to preclude smaller diameter surgical instruments from intruding between standoffs 950.

The combined effect of attachment mechanism 963, flange portion 967, and bias member 969 is the control by stand off assembly 940 of the movement of smaller diameter surgical instruments when forces having a generally orthogonal orientation to the longitudinal axis are employed as well as the ability of stand off assembly 940 to automatically accommodate larger diameter instruments.

Figure 19:
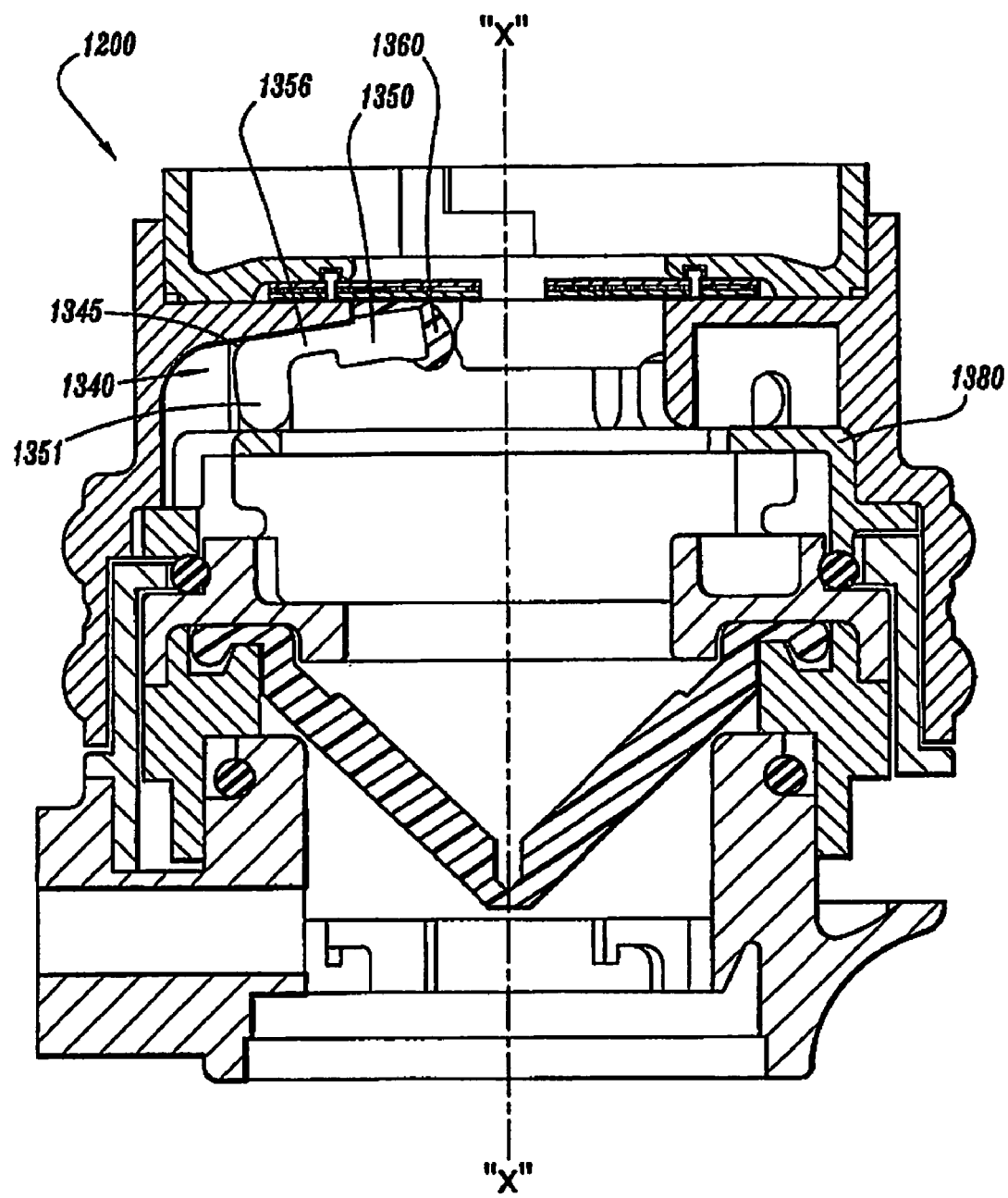
FIG. 19 is a cross-sectional side view of a fourth embodiment of the valve assembly and diameter reduction structure constructed in accordance with the present disclosure.

In FIG. 19, an additional preferred embodiment of valve assembly and diameter reduction structure 1200 is configured with a diameter reduction structure 1340 including a stand off assembly 1345 having four diametrically opposed stand off members, stand off elements, or simply stand offs 1350 independently positioned within a diameter reduction structure foundation 1380. Each stand off 1350 independently pivots, without a linking mechanism, to limit off-axis and angular movements of small instruments, such as a surgical object.

Stand off members 1350 include a head 1360, an arm 1356, and a base element 1351 configured for mounting with foundation 1380. Stand off 1350 can be fixedly mounted to foundation 1380 or example, or in the alternative base element 1351 may be pivotally positioned on foundation 1380 and retained in place using a positioning element (not shown). A bias is employed to position stand off 1380 to a first position adjacent housing 1310. As a further alternative embodiment, a linking mechanism may be positioned to be operative with heads 1360 to perform, for example, one or both functions of the linking mechanism shown previously. Alternative head 1360 configurations include having telescoping, tongue and grooved, or beveled gear mechanisms that interrelate stand offs 1380 into an approximately contiguous annular structure throughout their range of motion.

A bias inherent in stand off 1350 or in combination with its positioning element to the diameter reduction structure foundation 1380 maintains stand offs 1350 in the first position unless deflected by a large diameter surgical instrument. As shown in other embodiments, diameter reduction structure 1350 may be employed proximal to or distal to a first seal. Stand offs 1350, in this configuration, also include a bulbous shaped head 1360, similar to that of head 260 for controlling the movements of smaller diameter surgical instruments.

Figure 20A:
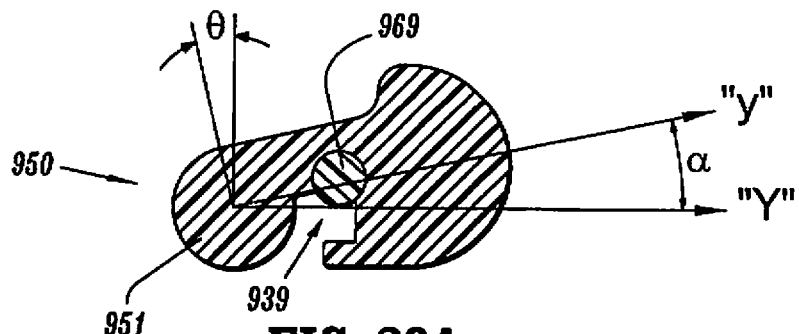
FIG. 20A is an enlarged cross-sectional view of the second embodiment of the stand off configuration of the diameter reduction structure for trocar of FIGS. 18A, 18B, and 18C.
Figure 20B:
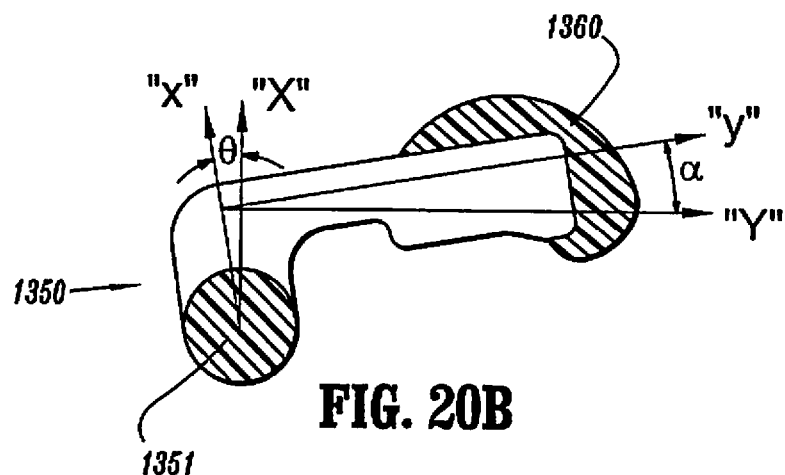
FIG. 20B is an enlarged cross-sectional view of the stand off configuration of the diameter reduction structure for trocar of FIG. 19.

In FIGS. 20A and 20B, two embodiments of stand off members 950 and 1350 are shown corresponding to FIGS. 18A-18C and 19, respectively. These two major configurations of stand offs, however, are only to be considered to be representative of all the stand off configurations described herein. Stand off members 950 and 1350 include base portions 951 and 1351 forming an axis "y" at angle alpha ($\alpha$) with an axis "Y". Axis "Y" is perpendicular to central longitudinal axis "X". Heads 960 and 1360 define an axis "x" at an angle theta "$\theta$" with the "X". Depending upon the configuration of the trocar housing and application, angles "$\alpha$" or "$\theta$" may be coincident with their respective "Y" and "X" axes or extend to the opposing side of their respective axes in alternative embodiments of stand offs 950 and 1350. Axis "X" is parallel to central longitudinal axis "X".

All the stand offs described herein provide a generally compression resistant biased structure against forces acting in a plane having a generally orthogonal orientation to the "X" or central longitudinal axis. It is envisioned that stand offs 950 and 1350, as well as all the other stand off variations herein are configured and positioned relative to structures such as the diameter reduction housings to at least provide a generally compression resistant biased structure against forces in planes at angles ranging from plus or minus approximately 15 degrees from an angle orthogonal to the central longitudinal axis.

Individual stand off members 950 and 1350 can include varying head portion 960 and 1360 configurations such as wing extensions or flanges that overlap, interrelate, or interleave between adjacent stand offs 950 and 1350. A retention mechanism 939 can also be included in head portion 960 and 1360, for example, for the positioning of a biased member 939.

Figure 20C:
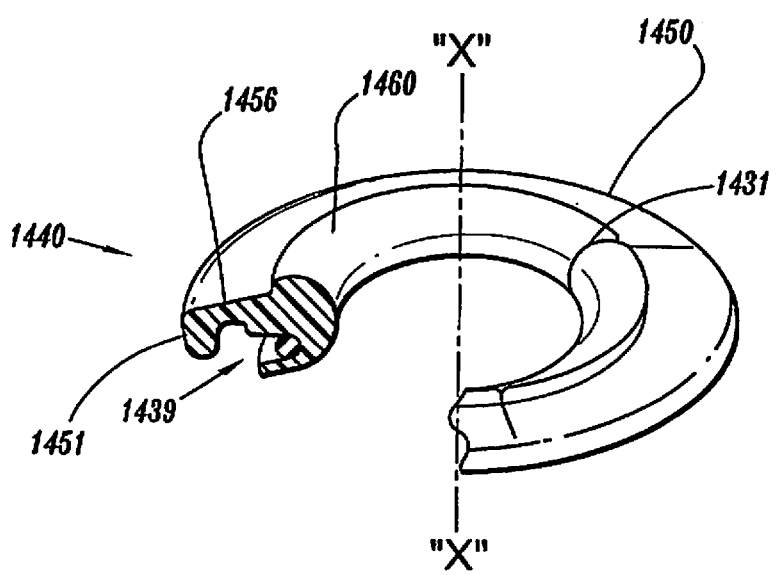
FIG. 20C is partial cross-sectional perspective view of a fifth embodiment of a diameter reduction structure constructed in accordance with the present disclosure.

Referring now to FIG. 20C, in a further alternate embodiment of a diameter reduction structure 1440, a single unified stand off assembly 1445 is formed into a continuous and integrated flanged stand off or flange structure 1445. Flange structure 1445 may take any configuration of head 1460, arm 1456, and base 1451, for example, suitable for performing the function of limiting the movement of smaller diameter surgical instruments when moved generally parallel off-axis or angularly. Diameter reduction structure 1440 may be at least partially segmented with a plurality of slots 1431 defining segmented head portions 1460 and arms 1456. A retention mechanism 1439 can also be employed to further bias diameter reduction structure 1440. This embodiment could also take the structural form of a cantilevered generally linear flexible flange structure or an angled stand off structure at least partially cantilevered and supported by a correspondingly positioned structure housing.

Diameter reduction structure 1440, with independent stand offs 1450 or configured as an integrated unified flange structure stand off 1450, is suitably configured to resist forces in a plane transverse to central longitudinal axis "X" and in particular forces in a plane approximately orthogonal to the central longitudinal axis "X". Flange structure 1450 is configured to flex or pivot with forces generally aligned with the longitudinal axis "X" so as to accommodate large diameter surgical instruments without any operational adjustments.

In another alternate embodiment the diameter reduction structure is a unified structure wherein the arms are joined to form an annular type structure configuration and are positioned within the trocar housing as an assembly. The stand off assembly in this embodiment can also include separate or integral biased members.

In still another embodiment, one or more diameter reduction structures could be employed together in series or in one assembly to create parallel diameter reduction structures or diameter reduction structures of different diameters.

Referring now to FIGS. 21 and 22A, a further alternate embodiment of a valve assembly and diameter reduction structure 1500 includes a diameter reduction assembly 1600 and valve assembly 1700. Valve assembly and diameter reduction structure 1500 defines a passageway 1505 concentric with a central longitudinal axis-X.

Diameter reduction assembly 1600 includes a first seal 1525, diameter reduction structure housing or distal housing 1610, a diameter reduction structure 1640, and a diameter reduction structure foundation element 1680. Diameter reduction structure foundation 1680 connects with valve assembly 1700. Seal housing or proximal housing 1710 of valve assembly 1700 is configured to be removably connected to cannula 50.

Diameter reduction structure housing 1610 is generally tubular in shape and includes a tubular wall 1615 defining a distal end portion 1612 and a proximal end portion 1614. Proximal end portion 1614 has a proximally extending rim 1616 defining a recessed portion or flange 1618. Flange 1618 is approximately perpendicular to the longitudinal axis-X and includes a rim 1619 defining a hole or passageway 1505 aligned with longitudinal axis-X. Diameter reduction structure housing 1610 in this configuration includes a first seal 1515 positioned distal to flange 1618 that is held in position by a first seal support element 1620. First seal support element 1620 also defines a rim 1622 aligned with rim 1619. A distal end of rim 1622 forms an edge 1623 with a distal end 1622 of seal support element 1620. Distal end portion 1612 includes a flanged portion 1613.

The inside diameter of tubular wall 1615 abuts and is configured to slidingly move in relation to a first member 1630 and a second annular member 1635. A distal edge 1631 of annular member 1630 is positioned abutting a proximal edge 1636 of second annular member 1635. Second annular member 1635 has a radially extending protuberance or tab 1637.

Diameter reduction housing 1610 is connected to an annular member 1611 extending distally from distal end 1612. A stop 1608 is positioned on a distal end 1609 of member 1611 that abuts a seal support element 1750 and defines a first position of housing 1610. Stop 1608 also interfaces with and is limited by tab 1637 to at least partially limit the proximal travel of housing 1610 and defines a second position of housing 1610.

Diameter reduction structure 1640 is positioned on a diameter reduction foundation element 1680. Diameter reduction foundation element 1680 has a distal end 1682 and a proximal end 1684. Distal end 1682 abuts with seal support element 1750. Element 1680 also abuts with a portion of the inside of annular members 1630 and 1635. Diameter reduction structure 1640 is configured to support up to approximately 180° of travel of each stand off member 1650 from a position extending distally approximately parallel to the longitudinal axis to a position extending proximately approximately parallel to the longitudinal axis.

In a first stand off assembly 240 position, stand off members 250 are generally positioned in a plane orthogonal the central longitudinal axis and to reduce the operable area of passageway 1505 in combination with the structural support of housing 1610. In a second stand off assembly 240 position, stand off members 250 are generally positioned at least partially distal to the first position. In a third stand off assembly 240 position, stand off members 250 are generally positioned at least partially proximal to the first position.

Stand off members 1650 have a head 1660 connected by an arm 1656 to a base portion 1651 with opposing cylindrical end portions 1654. Stand off members 250 are connected by a linking mechanism including three linking members 1671 as described in earlier embodiments.

Head 1660 includes a first side 1662 having a generally planar face and an opposing tapered second side 1668 in apposition with first seal 1525 when diameter reduction structure 1640 is in the first position. First side 1662 includes a cantilevered extension 1661. A third side 1664 includes a generally convex portion and beveled side portions 1665. A fourth side 1666, opposing, the third side, has a generally planar face that is connected with arm 1656 such that the planar face extends to second side 1662 and to cantilevered portion 1661. Arm 1656 is a neck down portion connecting base 1651 and head 1660. Head 1660 also includes a centrally positioned segmented concave notch 1663 approximately perpendicular to longitudinal axis-Y. The generally concave shape of notch 1663 is configured and dimensioned to accommodate a limited degree off axis movement by small surgical tools when diameter reduction structure 1640 is in a first or initial position.

While diameter reduction structure 1640 is illustrated with stand off assembly 1645 having three stand offs 1650 and linking mechanism 1670 having three linking members 1671, the general configuration of diameter reduction structure foundation 1680 and linking members 1671 are structurally and operationally similar to earlier embodiments such as those of FIGS. 6-8.

Valve assembly 1700 includes a first seal support member 1,750, a second seal 1765, and a seal housing 1710 configured for connecting to cannula 50. In addition, an elastic tubular seal or third seal 1601 is sealingly positioned over a sliding joint 1699 between valve assembly 1700 and diameter reduction assembly 1600.

Second seal support element 1750 is positioned between diameter reduction foundation element 1680 and seal housing 1710. Second seal support element 1750 has a generally annular in shape with a tubular wall 1755 having an outside cylindrical surface 1756. In addition, a distal end 1752 of second seal support element 1750 seals second seal 1765 in position in combination with a proximal end 1714 of seal housing 1710.

Seal housing 1710 proximal end portion 1714 includes positions for the seating of the second seal support element 1750 and second seal 1765. A distal end portion 1712 of seal housing 1710 is configured to mate with cannula 50 utilizing a suitable attachment mechanism such as a bayonet or threaded connection.

Third or tubular seal 1601 has a proximal end 1605 and a distal end 1603. Proximal end 1715 is sealingly engaged with flange 1613 of diameter reduction housing 1610. Proximal end 1714 of seal housing 1710 and distal end 1752 of second seal support element 1750 are positioned to sealingly engage a distal end portion 1603 of third seal 1601. Third seal 1601 is configured and dimensioned as a flexible elastic tubular seal positioned over and providing a seal for sliding joint 1699. Third seal 1601 is suitably flexible for accommodating the movement of diameter reduction housing 1610 between the first position wherein stop 1608 is abutting second seal support element 1750 and the second position wherein stop 1608 is repositioned proximally and is abutting tab 1637. In addition, third seal 1601 provides a bias to the first position of diameter reduction housing 1610 of seal housing 1610.

Figure 23:
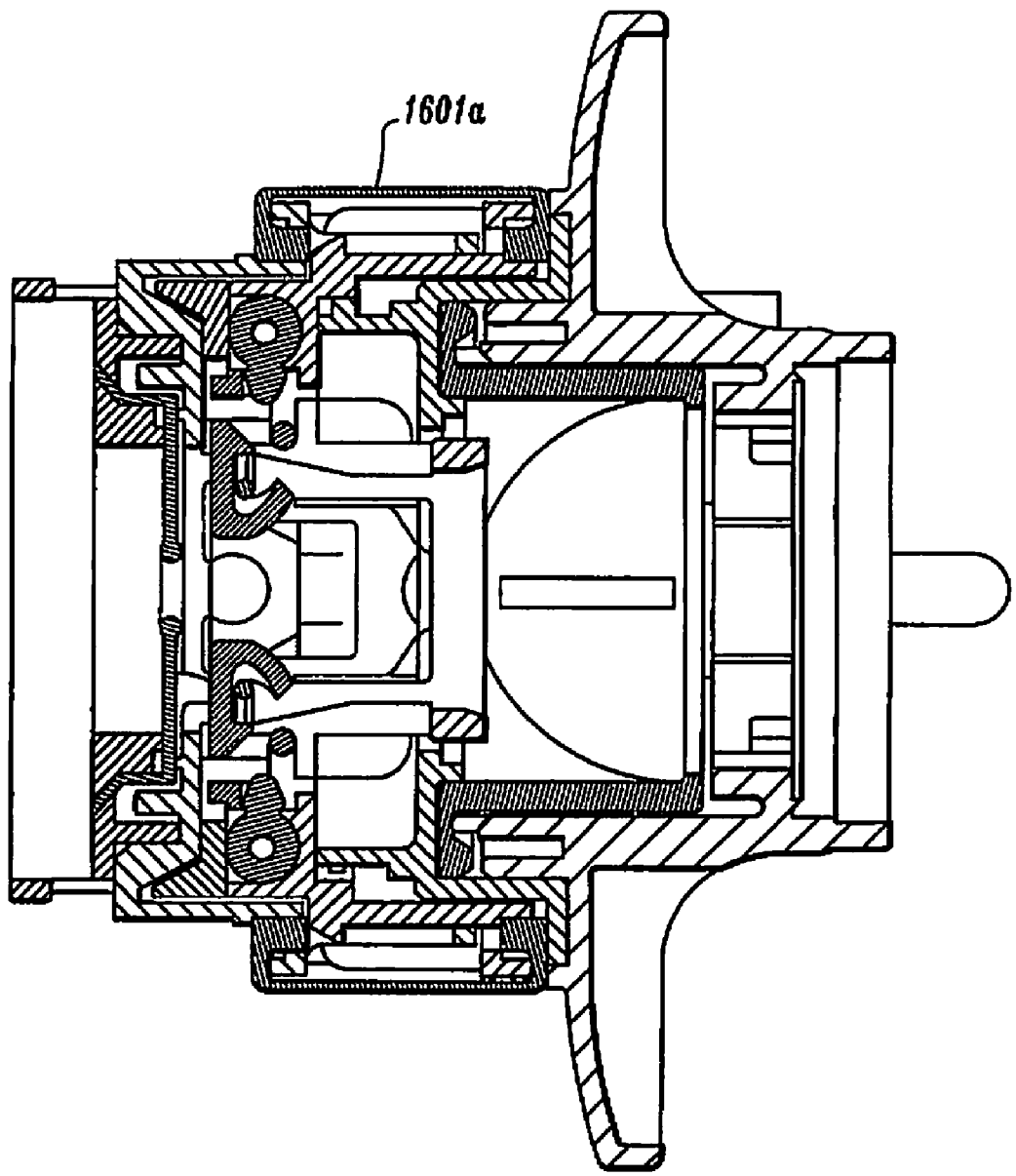
FIG. 23 is a cross-sectional view of an alternate embodiment of the valve assembly and diameter reduction structure of FIG. 22A.

Third seal 1601 is preferably fabricated from a flexible and/or stretchable material preferably an extrudable or injected moldable material, most preferably an elastomer or elastomeric or elastomer material. Third seal 1601 may include a central shape indentation 1601a to permit longitudinal extension and retraction of structure housing 1610. Alternatively, third seal may be completely tubular devoid of v-shape indentation as depicted in FIG. 23, and have suitable elastomeric properties to permit the seal to stretch during extension and retraction of the housing 1610. An elastomer material having a suitable thickness for external instrument applications that can encounter rugged handling and is resistant to tearing or penetration, for example, while providing a flexible bias. It is also envisioned that third seal 1601 can be readily attached and detached, as required, for autoclaving or sterilization.

Figure 22B:
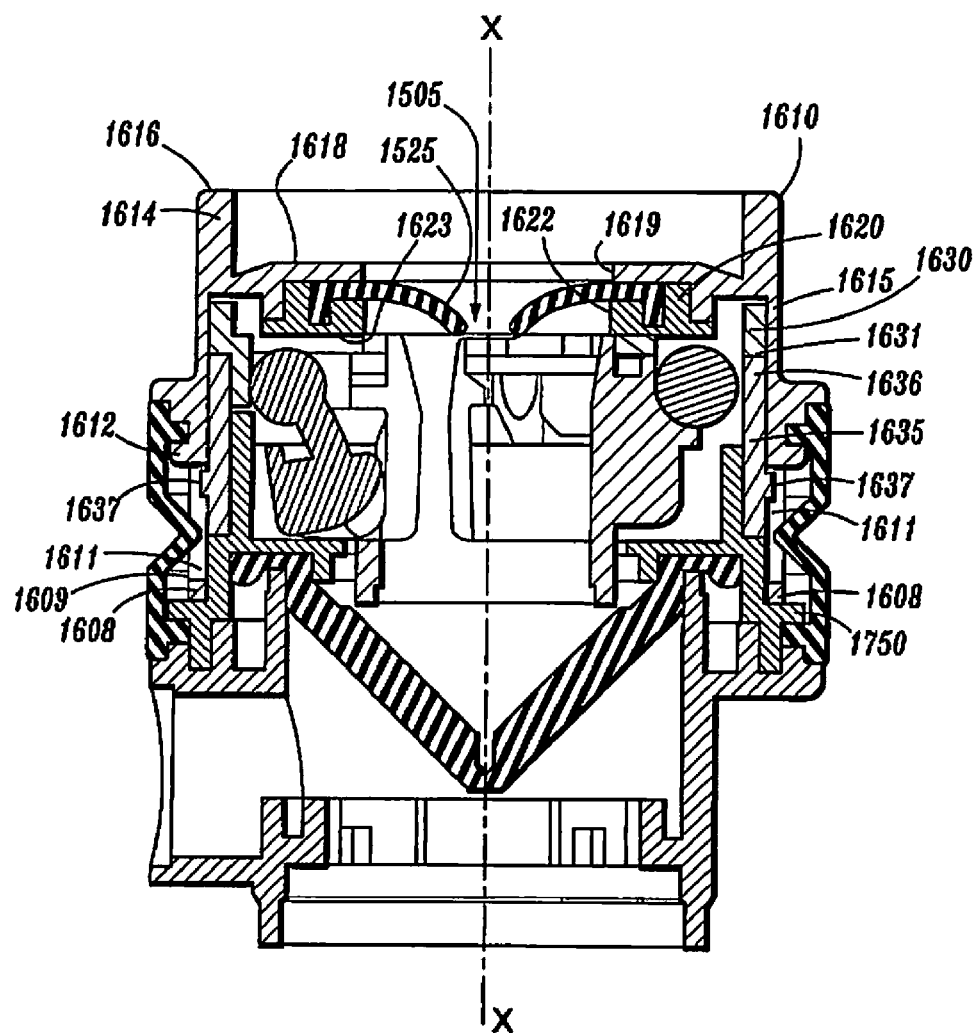
FIG. 22B is the cross-sectional view of the valve assembly and diameter reduction structure for trocar of FIG. 22A with the stand off assembly in the second position.
Figure 22C:
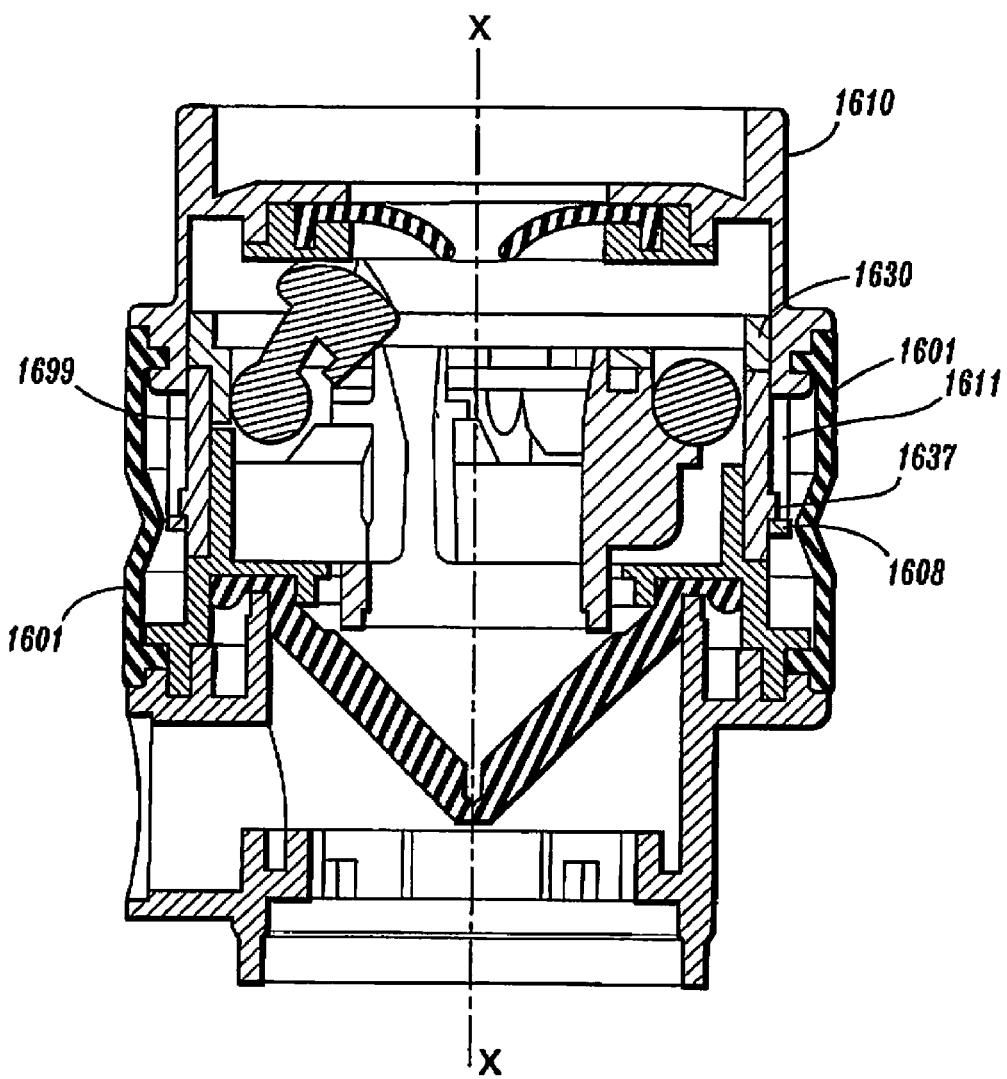
FIG. 22C is the cross-sectional view of the stand off configuration of FIG. 22A with the stand off assembly in a third position.

Referring now to FIGS. 22A-22C, diameter reduction structure 1640 is biased to a first position, similar to that of FIGS. 15, 16A, and 20A wherein at least a portion of fourth side 1666 of head 1660 and arm 1656 are in apposition with a portion of diameter reduction structure housing 1610 and stop 1608 is abutting second seal support element 1750. In this embodiment, rim 1621 and distal end 1622 of first seal support element 1620 are in apposition with at least a portion of fourth side 1666 and arm 1656, respectively and in particular, corner 1623 is positioned at the junction of arms 1656 and side fourth side 1666. Thus, first seal support element 1620 supports stand offs 1650 in the first position by providing structural support for stand offs 1650 to limit from the off axis and angular movements of small diameter surgical instruments.

When diameter reduction structure 1640 is deflected distally by a large surgical instrument, such as shown in FIG. 13, to the second position wherein face 1662 is pivoted in the direction of the inside of tubular wall 1755 of second seal support element 1750, stand off members 1650 are accommodating the increased diameter of the large surgical instrument without any external adjustments by the surgeon or operator. Stand off members 1640, however; retain their bias to the first position.

When the large surgical instrument is withdrawn proximally through valve assembly and diameter reduction structure 1500, the combination of the bias and elastic nature of stand off members 1650 may bind with the large instrument. To preclude undesirable binding, distal end 1612 is slidingly engaged with first annular member 1630, second annular member 1635, and second seal support element 1750 such that the diameter reduction housing 1610 slides proximally until the instrument ceases to bind or stop 1608 abuts tab 1637. The proximal movement of diameter reduction structure 1610 from the first housing 1610 position defines an increased volume within diameter housing 1610 that is suitable for stand off members 1650 to pivot proximally to the third position and at least partially increase the operable area of passageway 1505 from the second operable area to a third operable at least wherein the operable area is increased similar to that of the second position of the stand off assembly such that the large instrument can be withdrawn with limited resistance.

Additional alternative embodiments for precluding binding include a catch or an engaging receptacle for each stand off in the second position with an external release mechanism, for example, or a friction reducing means such as one or more wheels positioned on second side 1668 and/or third side 1664 that could accommodate the withdrawal of the large instrument while in a distal or second position by the rotation of the wheel and still provide adequate resistance to movements of small surgical instruments when in the first position.

Figure 24:
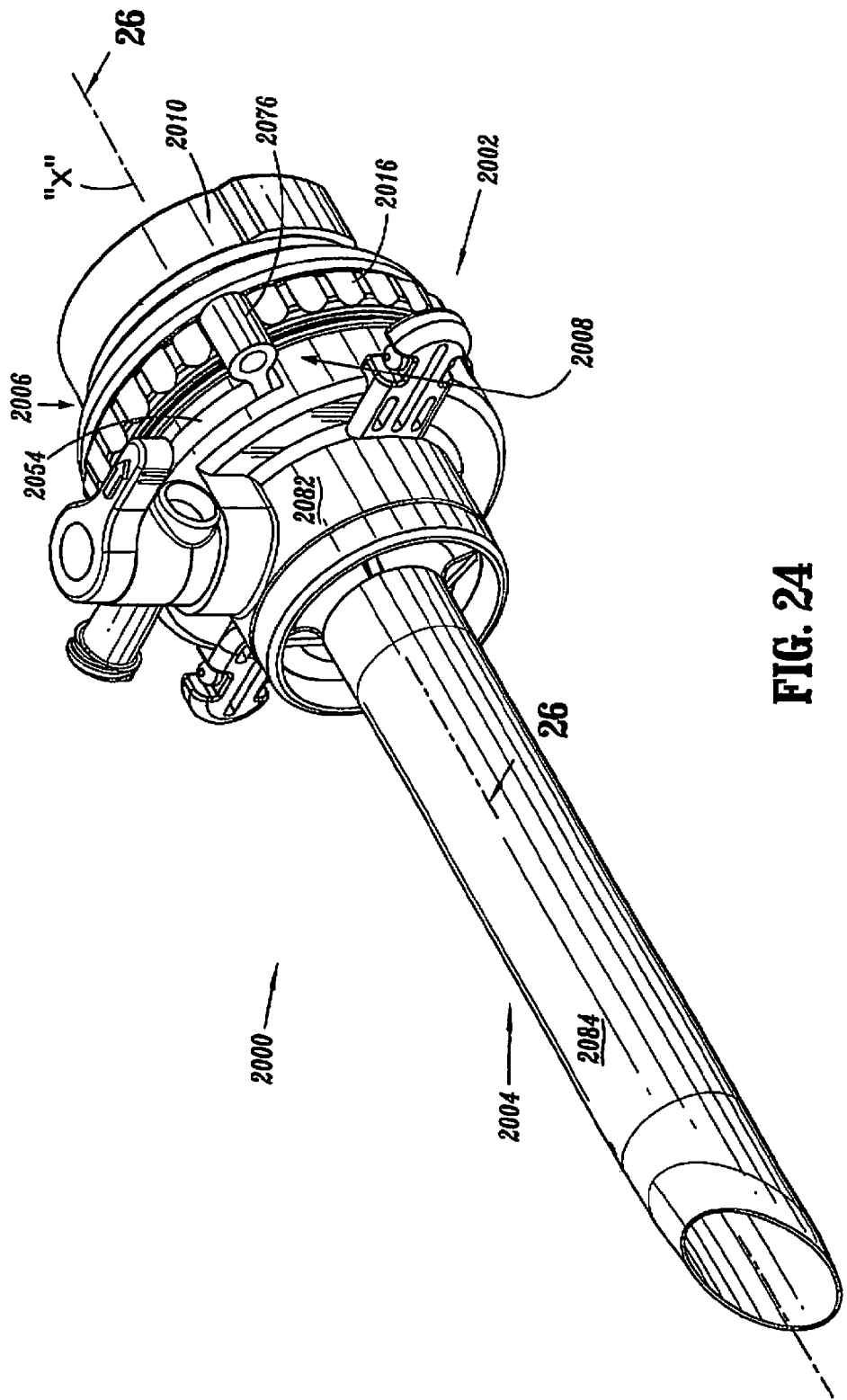
FIG. 24 is a perspective view of another alternate embodiment of the seal assembly shown mounted to a cannula assembly in accordance with the principles of the present disclosure.

Referring now to FIG. 24, there is illustrated another embodiment of the present disclosure. System 2000 includes seal assembly 2002 and cannula assembly 2004 to which the seal assembly 2002 is mounted. Seal assembly 2002 defines a seal housing consisting of a plurality of components forming an outer member of the seal assembly 2002, and diameter reduction structure for limiting excessive off-axis and angular movements of small diameter surgical instruments as discussed hereinabove. Seal assembly 2002 defines seal axis "x". Seal assembly 2002 includes first or proximal seal subassembly 2006 and second or distal seal subassembly 2008 which is connected to cannula assembly 2004. First seal subassembly 2006 is adapted for releasable connection to second seal subassembly 2008 and incorporates the diameter reduction structure.

Figure 25:
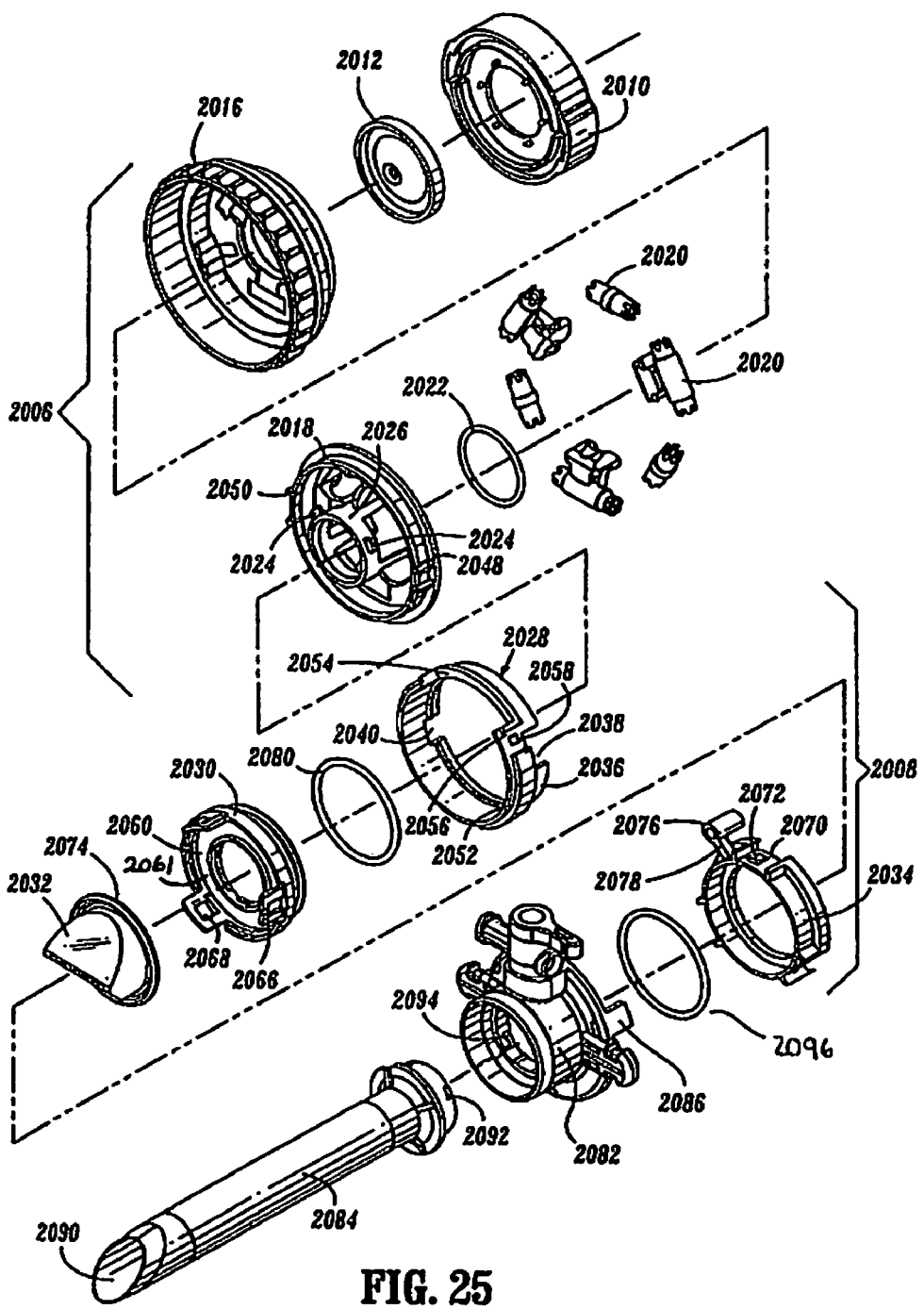
FIG. 25 is a perspective view with parts separated of the seal assembly and cannula assembly in accordance with the embodiment of FIG. 24 illustrating the components of the first and second seal subassemblies.
Figure 26:
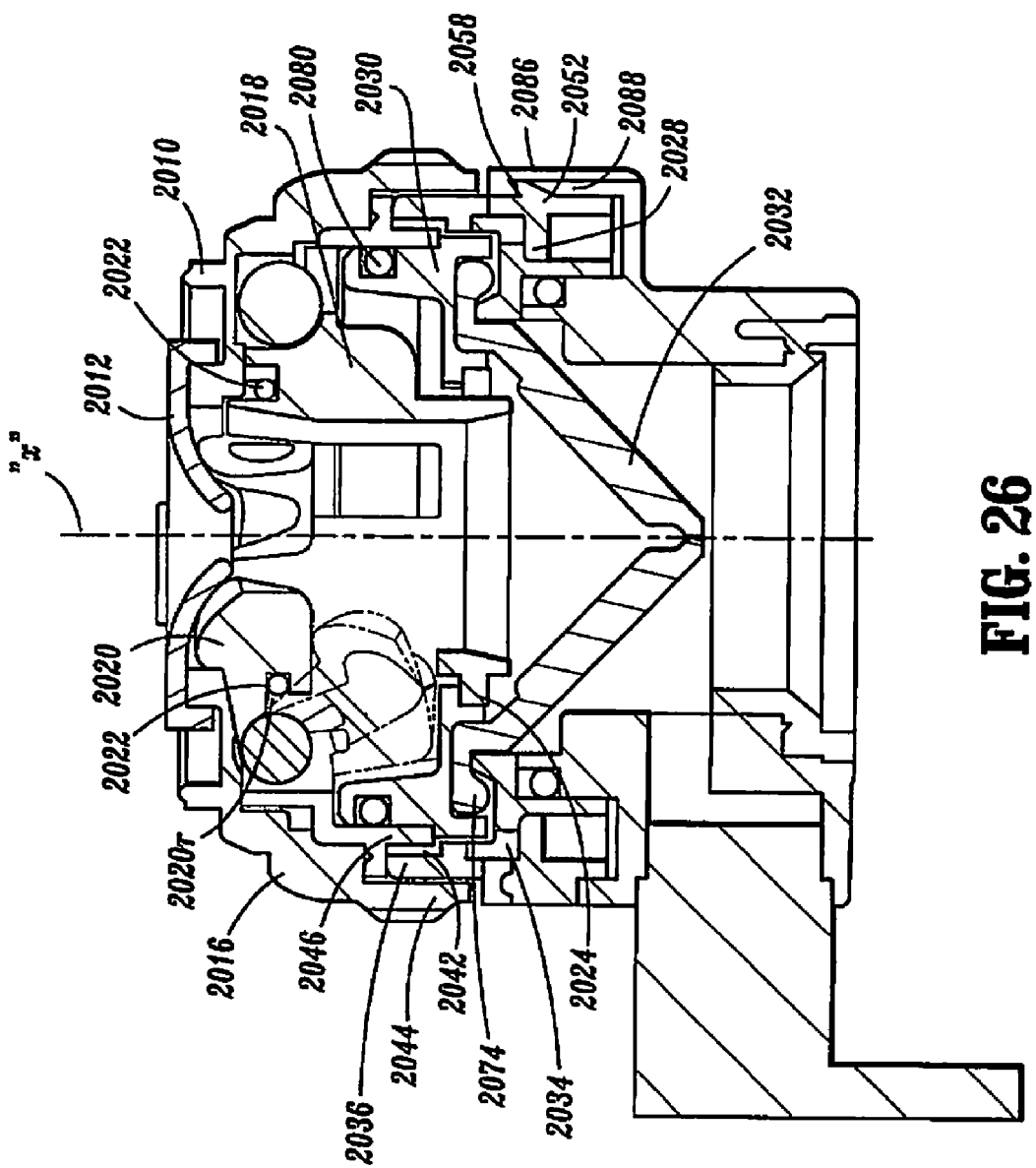
FIG. 26 is a side cross-sectional view taken along the lines 26-26 of FIG. 24 illustrating the seal assembly mounted to the cannula housing of the cannula assembly in accordance with the embodiment of FIGS. 24-25.
Figure 27:
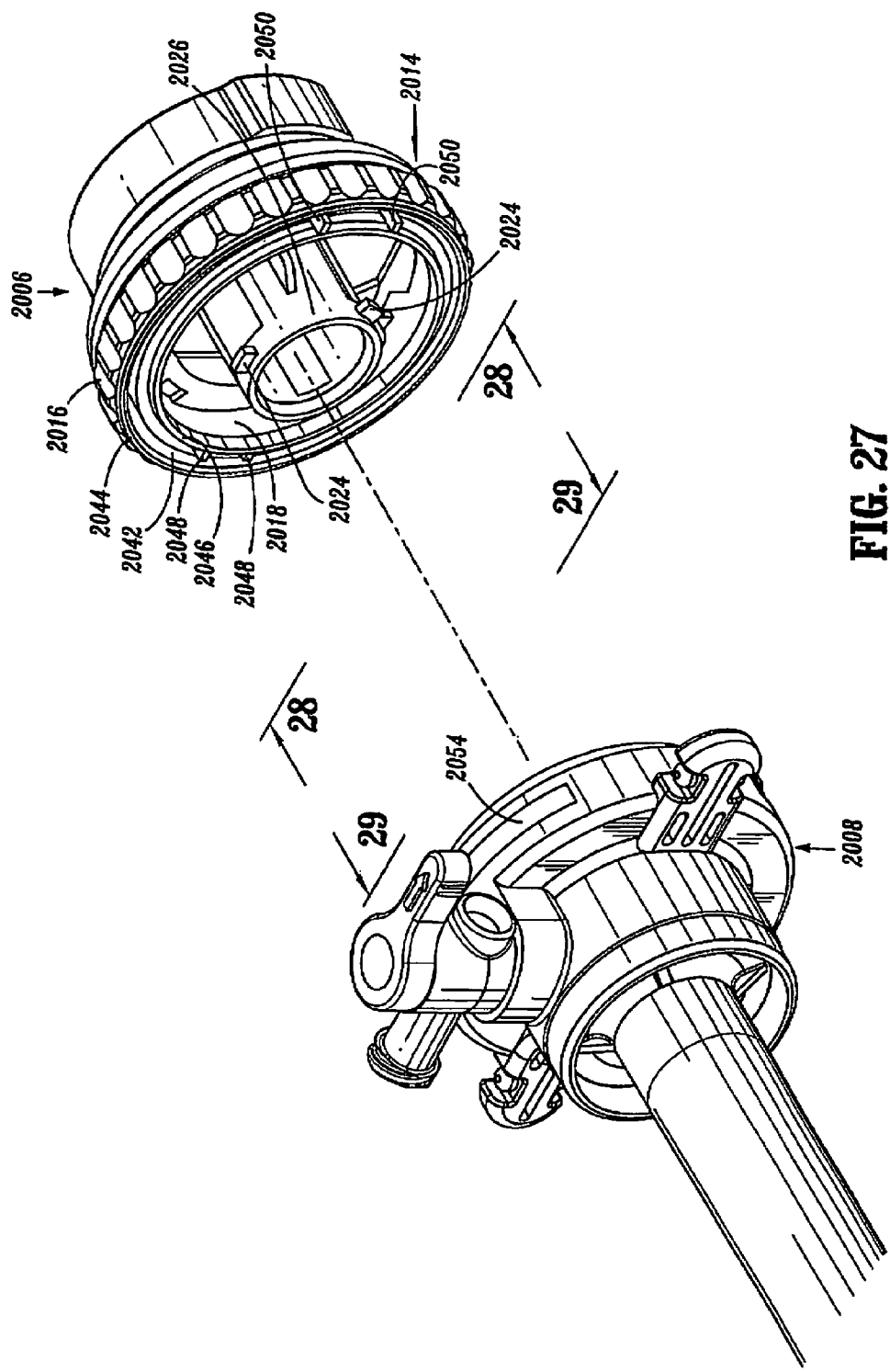
FIG. 27 is a perspective view illustrating mounting of the first seal subassembly to the second seal subassembly in accordance with the embodiment of FIGS. 24-26.

With reference now to FIG. 25-27, in conjunction with FIG. 24, first and second seal subassemblies 2006, 2008 of seal assembly 2002 will be discussed. First seal subassembly 2006 includes end cap 2010, septum seal 2012 and diameter reduction housing 2014. Diameter reduction housing 2014 includes first and second reduction housing components 2016, 2018 which house stand-off elements 2020. In general, stand-off elements 2020 are interconnected and pivot to permit passage of an instrument. Stand-off elements 2020 are biased to an initial position by elastomeric O-ring 2022. O-ring 2022 is received within recess 2020r of each stand-off element 2020 as shown in FIG. 26. When stand-off elements 2020 pivot downwardly (shown in phantom in FIG. 26) upon insertion of an instrument, O-ring 2022 stretches to permit this movement of the stand-off elements 2020. Upon removal of the instrument, the stand-off elements 2020 return to their initial position in transverse relation to the axis "x" under the influence of the O-ring 2022. The remaining components of first seal subassembly 2006 are substantially similar to their corresponding components disclosed and discussed in the prior embodiments, and reference is made hereinabove for a further discussion of the structure and functionality of these components.

In one further aspect of the present embodiment, diameter reduction housing 2014 includes a plurality of mounting tabs 2024 radially spaced about interior wall 2026 of second reduction housing component 2018. As seen in FIG. 25 and FIG. 27, mounting tabs 2024 serve to releasably secure first seal subassembly 2006 to second seal subassembly 2008 as will be discussed.

Second seal subassembly 2008 includes stationary ring member 2028, duckbill valve housing 2030, zero closure or duck bill valve 2032 supported within the valve housing 2030, and manual lock member 2034. Stationary ring member 2028 defines first annular wall 2036 on its proximal side. Annular wall 2036 incorporates small and large recesses 2038, 2040 arranged in diametrical opposed relation as shown. First annual wall 2036 of stationary ring member 2028 is received within annular gap 2042 defined between walls 2044, 2046 of first and second reduction housing components 2016, 2018, respectively (FIG. 26). Small and large recesses 2038, 2040 receive corresponding pairs of positioning legs 2048, 2050 of reduction housing 2014. As best depicted in FIGS. 28 and 29, the respective distances between the positioning legs 2048, 2050 and corresponding lengths of recesses 2038, 2040 (identified as distances and lengths "a" and "b") ensure proper orientation of reduction housing 2014 within, or relative to, stationary ring member 2028 during assembly.

Stationary ring member 2028 further includes second annular wall 2052 disposed on the distal side of the stationary ring member 2028. Second annular wall 2052 includes partial annular slot 2054 therein and a plurality of radially spaced grooves 2056 in its outer surface. A single locking tab 2058 is disposed within each groove 2056. The functioning of partial slot 2054, spaced grooves 2056 and locking tabs 2058 will be discussed in greater detail hereinbelow.

As best depicted in FIGS. 25 and 29, duck bill valve housing 2030 includes annular wall 2060 which defines central aperture 2062. Annular wall 2060 defines three grooves 2064 proximal aperture 2062. Grooves 2064 accommodate mounting tabs 2024 of diameter reduction housing 2014 during assembly of first and second seal subassemblies 2006, 2008. Duck bill housing 2030 includes a plurality of axial depending legs 2066. Legs 2066 of duck bill valve housing 2030 may include rectangular openings 2068.

In one preferred arrangement, manual lock member 2034 is secured to duck bill housing 2030 in fixed relation therewith. Manual lock member 2034 includes a plurality of recesses 2070 defined in its outer surface. Recesses 2070 receive corresponding depending legs 2066 of duck bill housing 2030. Recesses 2070 each include mounting tabs 2072 (as seen in FIG. 25) which are received within rectangular openings 2068 of depending legs 2066 of duck bill housing 2030 in snap relation therewith to secure the two components (see also FIG. 26). Manual lock member 2034 and duck bill housing 2030 capture the peripheral rim 2074 of duck bill valve 2032 to secure the duck bill valve 2032 between the two components.

Manual lock member 2034 and duck bill housing 2030 are at least partially disposed within stationary ring member 2028 and are adapted for rotational movement relative to the stationary ring member 2028. Manual lock member 2034 includes grip 2076 which extends radially outwardly such that at least a portion of the grip 2076 is positioned externally of the stationary ring member 2028 for engagement by the user. Grip 2076 includes transverse leg 2078 which is accommodated within partial annular slot 2054 of stationary ring member 2028 and traverses the slot 2054 during rotation of manual lock member 2034 and duck bill housing 2030. Manual lock member 2034 is adapted for rotational movement between a first position corresponding to a release position which permits mounting and/or release of first subassembly 2006 from second subassembly 2008, and a second position corresponding to a lock position which secures first subassembly 2006 to the second subassembly 2008. An O-ring seal 2080 may be positioned about the circumference of duck bill housing 2030 to form a substantial seal between the duck bill housing 2030 and diameter reduction housing 2014.

In other embodiments, the manual lock member 2034 is slidably received by duck bill housing 2030. The manual lock member 2034 is then slidable with respect to stationary ring member 2028.

With reference to FIGS. 24-26, cannula assembly 2004 includes cannula housing 2082 and cannula sleeve 2084 extending from the housing 2082. Cannula housing 2082 includes vertical legs 2086 which are positioned within grooves 2056 of stationary ring member 2028. Legs 2086 preferably include internal ledges 2088 advantageously dimensioned to accommodate locking tabs 2058 disposed within the grooves 2056 of stationary ring member 2028 to fixedly secure the two components. Cannula sleeve 2084 defines longitudinal passage 2090 which permits passage of instrumentation. Cannula sleeve 2084 may be secured to cannula housing 2082 by corresponding tongues 2092 and grooves 2094 of the cannula sleeve 2084 and the cannula housing 2082 respectively. An O-ring seal 2096 may be positioned within cannula housing 2082 for forming a seal within the housing 2082 adjacent these components.

Figure 31:
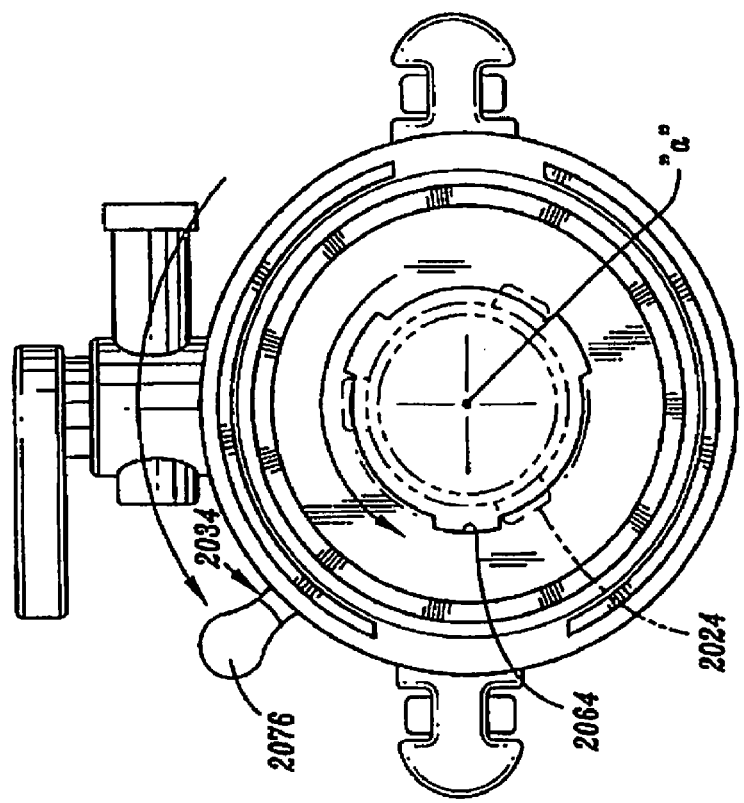
FIG. 31 is a view of the seal assembly illustrating the manual lock member in a second position corresponding to a locked position in accordance with the embodiment of FIGS. 24-30.
Figure 30:
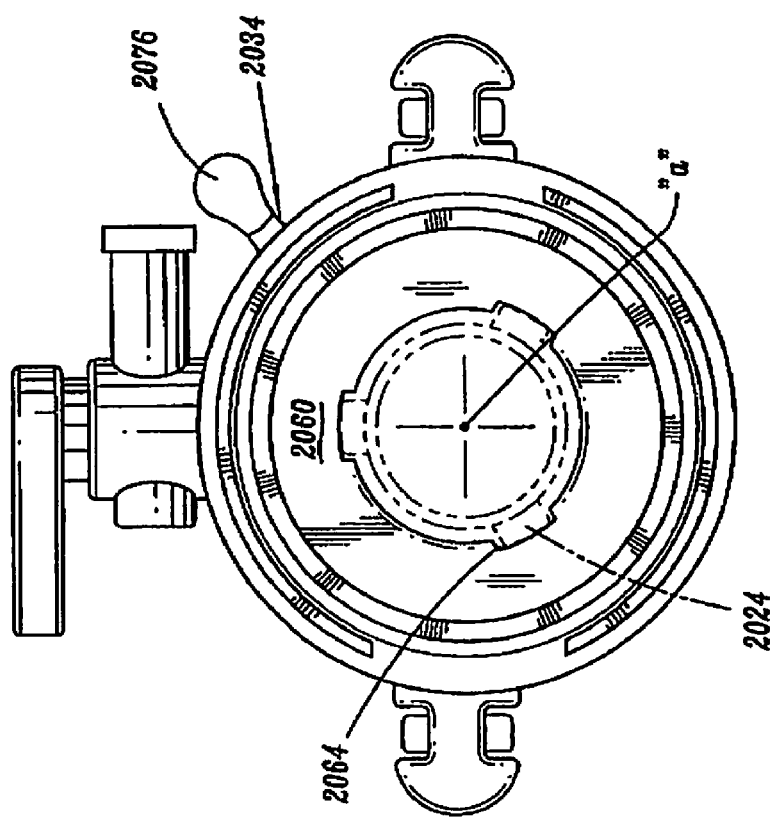
FIG. 30 is a view of the seal assembly illustrating the manual lock member in a first position corresponding to a release position in accordance with the embodiment of FIGS. 24-29.

In use, second seal subassembly 2008 of seal assembly 2002 is mounted to cannula housing 2082. In this regard, vertical legs 2086 of cannula housing 2082 are aligned with grooves 2056 of stationary ring member 2028 and the ring member 2028 is advanced whereby the locking tabs 2058 of the ring member 2028 securely engage the internal ledges 2088 within the vertical legs 2086. Thereafter, when it is determined that the diameter reduction structure is needed, for example, in use with a small diameter instrument, first seal subassembly 2006 is positioned relative to second seal subassembly 2008 as depicted in FIGS. 27-29. In this position, positioning legs 2048, 2050 of diameter reduction or first seal housing 2014 of first seal subassembly 2006 are aligned with the corresponding recesses 2038, 2040 of second seal housing or duck bill housing 2030 of second seal subassembly 2008 (FIGS. 25 and 27). In addition, manual lock member 2034 is placed in the first or release position of FIG. 29. In this position, mounting or locking tabs or locking latches 2024 of the first seal subassembly 2006 are in general alignment with mounting or locking recesses or grooves 2064 of the annular plate or annular member 2060 of duck bill housing 2030 of the second seal subassembly 2008. First seal subassembly 2006 is then mounted to second seal subassembly 2008 whereby positioning legs 2048, 2050 are positioned in respective recesses 2038, 2040 and mounting tabs 2024 are received within mounting grooves 2064 of duck bill housing 2030. Manual lock member 2034 is then rotated about axis "a" through an arc of at least thirty (30) degrees from the first or release position depicted in FIG. 30 to the second or lock position depicted in FIG. 31. This movement of manual lock member 2034 causes corresponding rotational movement of duck bill housing 2030 to displace the mounting grooves 2064 whereby mounting tabs 2024 are captured beneath annular wall 2060 of duck bill housing 2030, i.e., engaging the distal locking surface or face 2061 of annular wall 2060 (see also FIG. 25). In this position, first seal subassembly 2006 is secured to second seal subassembly 2008. The procedure is continued by introducing an instrument through the seal assembly 2002 and cannula assembly 2004, and performing the desired surgical procedure It is noted that duck bill housing 2030 and manual lock member 2034 may be a single component monolithically formed during manufacture. In addition, it is envisioned that the second seal subassembly 2008 may be a component of the cannula housing or sleeve housing 2082, and supplied with the cannula assembly 2004. In the alternative, second seal subassembly 2008 may replace the cannula housing 2082 in its entirety and serve as the sleeve housing. It is further envisioned that other modified first seal subassemblies, for example, with or without diameter reduction structure, may be adapted for use with the second seal subassembly 2008.

Although the illustrative embodiments of the present disclosure have been described herein with reference to the accompanying drawings, it is to be understood that the disclosure is not limited to those precise embodiments and that various other changes and modifications may be affected therein by one skilled in the art without departing from the scope or spirit from the disclosure. All such changes and modifications are intended to be included within the scope of the appended claims.

What is claimed is:

1. A surgical access device comprising:
   a surgical sleeve defining a central longitudinal axis and having a longitudinal passageway to permit passage of a surgical object; and
   a diameter reduction assembly operably couplable to the surgical sleeve, the diameter reduction assembly including:
      a structure foundation including a tubular wall, a first member, and a second annular member; and
      at least three stand-off elements mounted to the structure foundation about the longitudinal axis, each stand-off element being positioned to engage the surgical object during insertion and being independently movable relative to the remaining stand-off elements to permit passage of the surgical object, the at least three stand-off elements dimensioned and arranged to contact the surgical object and to minimize off-axis and/or angular movement of the surgical object,
   the at least three stand-off elements being normally biased to a first position which urges the surgical object into general alignment with the central longitudinal axis, each of the at least three stand-off elements being adapted for distal pivotal movement from the first position to a second position distal to the first position to facilitate passage of the surgical object, and each being further adapted for proximal pivotal movement from the first position to a third position proximal to the first position to facilitate withdrawal of the surgical object, the tubular wall of the structure foundation being adapted for longitudinal movement relative to the first member and the second annular member to increase an effective length of the structure foundation to accommodate the proximal pivotal movement of the at least three stand-off elements to the third position.

2. The surgical access device of claim 1, including a seal proximal of the at least three stand-off elements for establishing a substantial sealing relation with the surgical object.

3. The surgical access device of claim 1, including a seal distal of the at least three stand-off elements for establishing a substantial sealing relation with the surgical object.

4. The surgical access device of claim 1, wherein the diameter reduction assembly includes a fourth stand-off element, the four stand-off elements being radially spaced about the central longitudinal axis.

5. The surgical access device of claim 1, including a seal assembly having a seal housing and a seal for establishing a substantial sealing relation with the surgical object, the seal assembly configured to be detachably mountable to the surgical sleeve.

6. The surgical access device of claim 5 wherein the diameter reduction assembly is adapted for releasable mounting to the seal housing of the seal assembly.

7. The surgical access device of claim 1, wherein each stand-off element includes:
   a base configured for mounting within the diameter reduction structure foundation;
   a head adapted to form an interrupted annular structure with the heads of the other stand-off elements, the head being configured for controlling forces resulting from parallel off-axis and angular movements of a surgical object positioned therein in a plane generally orthogonal to the central longitudinal axis; and
   an arm connecting the base with the head.

8. The surgical access device of claim 7, wherein the interrupted annular structure is resistant to movement by forces in planes at angles of about 15° from an angle orthogonal to the central longitudinal axis.

9. The surgical access device of claim 7, wherein the head of each stand-off element is bulbous for controlling movement of the surgical object.

10. The surgical access device of claim 7, wherein when the at least three stand-off elements are each biased to the first position, an axis of the head of each stand-off element is displaced at an angle intersecting the central longitudinal axis.

* * * * *